(12) United States Patent
Zumeris et al.

(10) Patent No.: US 7,829,029 B2
(45) Date of Patent: Nov. 9, 2010

(54) ACOUSTIC ADD-ON DEVICE FOR BIOFILM PREVENTION IN URINARY CATHETER

(75) Inventors: Jona Zumeris, Haifa (IL); Harold Jacob, Cedarhurst, NY (US)

(73) Assignee: NanoVibronix, Inv., Nesher (IL)

( * ) Notice: Subject to any disclaimer, the term of this patent is extended or adjusted under 35 U.S.C. 154(b) by 883 days.

(21) Appl. No.: 11/730,005

(22) Filed: Mar. 29, 2007

(65) Prior Publication Data

US 2007/0244423 A1 Oct. 18, 2007

Related U.S. Application Data

(60) Provisional application No. 60/786,701, filed on Mar. 29, 2006.

(51) Int. Cl.
*A61L 2/025* (2006.01)

(52) U.S. Cl. .......................... 422/127; 422/20; 422/128; 600/466; 604/22

(58) Field of Classification Search ........................ None
See application file for complete search history.

(56) References Cited

U.S. PATENT DOCUMENTS

| 3,708,263 | A | 1/1973 | Boucher |
|---|---|---|---|
| 4,016,436 | A | 4/1977 | Shoh |
| 4,216,766 | A | 8/1980 | Duyhers et al. |
| 4,698,058 | A | 10/1987 | Greenfeld et al. |
| 4,841,977 | A | 6/1989 | Griffith et al. |
| 5,069,664 | A | 12/1991 | Guess et al. |
| 5,240,675 | A | 8/1993 | Wilk et al. |
| 5,271,735 | A | 12/1993 | Greenfeld et al. |
| 5,709,672 | A * | 1/1998 | Illner .......................... 604/265 |
| 5,725,494 | A | 3/1998 | Brisken |
| 5,728,064 | A | 3/1998 | Burns et al. |
| 5,904,659 | A | 5/1999 | Duarte et al. |
| 6,210,393 | B1 | 4/2001 | Brisken |
| 6,283,921 | B1 | 9/2001 | Nix et al. |
| 6,681,783 | B2 | 1/2004 | Kawazoe |

(Continued)

FOREIGN PATENT DOCUMENTS

EP 1 197 177 4/2002

(Continued)

OTHER PUBLICATIONS

Andrea M. Rediske et al, "Pulsed Ultrasound Enhances the Killing of *Escherichia coli* Biofilms by Aminoglycoside Antibiotics In Vivo", Antimcrobial Agents and Chemotherapy, vol. 44, No. 3, Mar. 2000, pp. 771-772.

(Continued)

*Primary Examiner*—Elizabeth L McKane
(74) *Attorney, Agent, or Firm*—Pearl Cohen Zedek Latzer, LLP

(57) ABSTRACT

A urinary catheter clip-on device applies surface acoustic waves of Rayleigh-Lamb and/or Love type to a urinary catheter for preventing biofilms on the catheter surfaces. The bacteria is forced to move relative to the vibrating catheter surface. The amplitudes of bacteria vibrations are in nanometer range. The relative motion of bacteria results in bacteria quorum sensing, and disrupts the bacteria attachment process. The method is preventive as surface acoustic waves create low acoustic energy and bacteria is not killed.

50 Claims, 21 Drawing Sheets

U.S. PATENT DOCUMENTS

| | | | |
|---|---|---|---|
| 2002/0065512 A1 | 5/2002 | Fjield et al. | |
| 2003/0065355 A1* | 4/2003 | Weber | 606/200 |
| 2005/0038376 A1 | 2/2005 | Zumeris et al. | |
| 2005/0148911 A1 | 7/2005 | Talish et al. | |

FOREIGN PATENT DOCUMENTS

| | | |
|---|---|---|
| JP | 2001-526926 | 12/2001 |
| JP | 2002-112963 | 4/2002 |
| WO | WO 9933391 | 7/1999 |

OTHER PUBLICATIONS

J.M. Schierholz et al., "Implant infections: a haven for opportunistic bacteria", Journal of Hospital Infection, vol. 49, pp. 87-93 (Oct. 2001).

P. Thibon et al., "Randomized multi-centre trial of the effects of a catheter coated with hydrogel and silver salts on the incidence of hospital-acquired urinary tract infections" Journal of Hospital Infection, vol. 45, pp. 117-124, Jun. 2000.

Wendy E. Thomas et al., "Bacterial Adhesion to Target Cells Enhanced by Shear Force", Cell, vol. 109, pp. 913-923, Jun. 28, 2002.

Marvin Whiteley et al., "Identification of genes controlled by quorum sensing in *Pseudomonas aeruginosa*", PNAS, Nov. 23, 1999, vol. 96, No. 24, pp. 13904-13909.

Alvin J. Yamamoto et al., "Sutureless Securement Device Reduces Complications of Peripherally Inserted Central Venous Catheters", J Vasc Interv Radiol., vol. 13, No. 1, 2002, pp. 77-81.

William G. Pitt et al., "Ultrasonic Enhancement of Antibiotic Action on Gram-Negative Bacteria", Antimicrobial Agents and Chemotherapy, vol. 30, No. 11, Nov. 1994, pp. 2577-2582.

Zhen Qian et al., "Investigation of the mechanism of the bioacoustic effect", J. Biomed Mater Res, vol. 44, pp. 198-205, 1999.

"Biological Effects of Ultrasound: Mechanisms and Clinical Implications" (N C R P Report No. 74), National Council on Radiation Protection and Measurements, (Dec. 30, 1983).

John C. Carmen et al., "Treatment of Biofilm Infections on Implants with Low-frequency Ultrasound and Antibiotics", Am J Infect Control., Mar. 2005; vol. 33, No. 2, pp. 78-82.

AG Gristina, "Biomaterial-centered infection: microbial adhesion versus tissue integration", Science, vol. 237, Issue 4822, pp. 1588-1595 (Sep. 25, 1987).

Kim Lewis, "Riddle of Biofilm Resistance", Antimicrobial Agents and Chemotherapy, vol. 45, No. 4, Apr. 2001, pp. 999-1007.

E Mahenthiralingam et al., "Nonmotility and phagocytic resistance of *Pseudomonas aeruginosa* isolates from chronically colonized patients with cystic fibrosis", Infect Immun., Feb. 1994, vol. 62, No. 2, pp. 596-605.

Dennis G. Maki et al., "Engineering out the Risk of Infection with Urinary Catheters", Emerging Infectious Diseases, vol. 7, No. 2, Mar.-Apr. 2001, pp. 1-6.

* cited by examiner

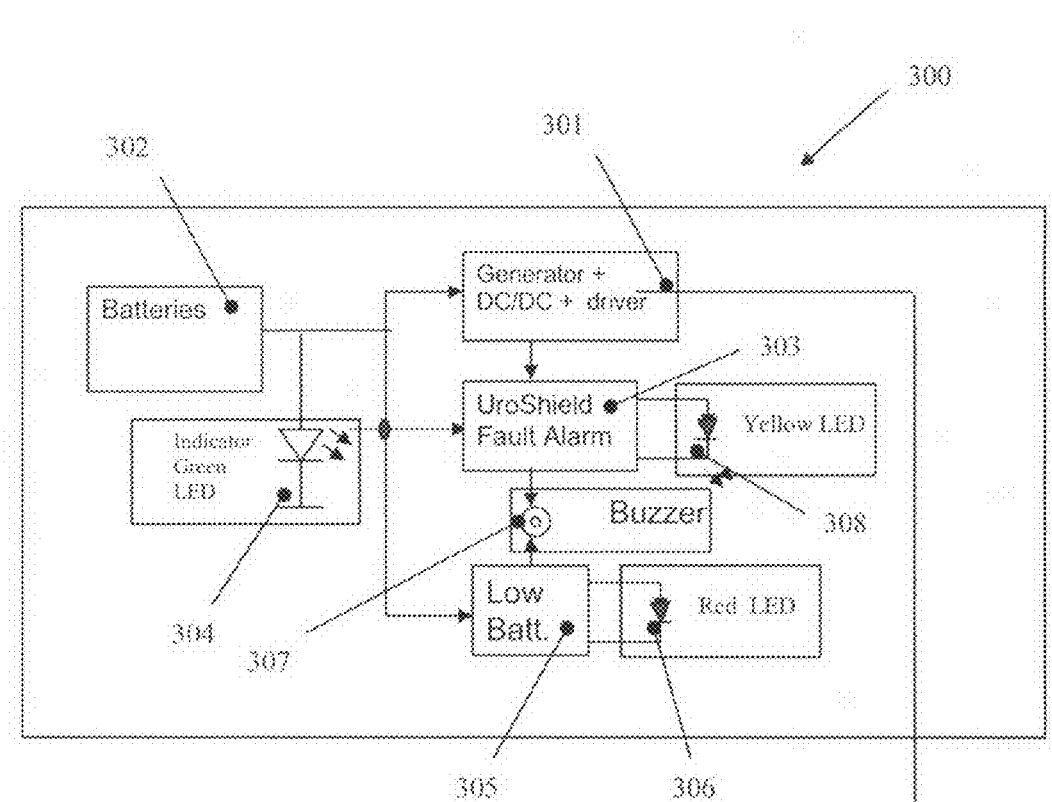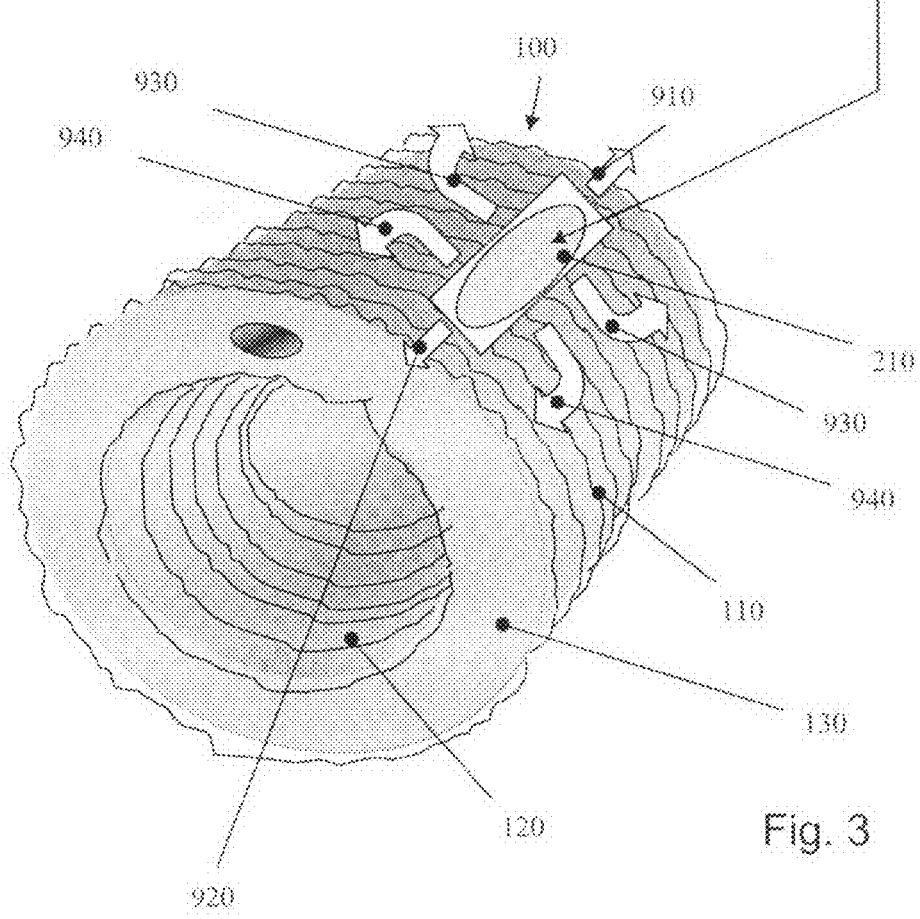
Fig. 3

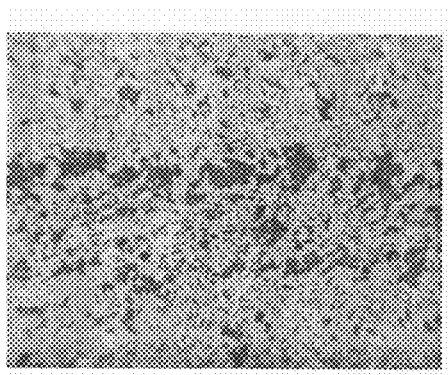
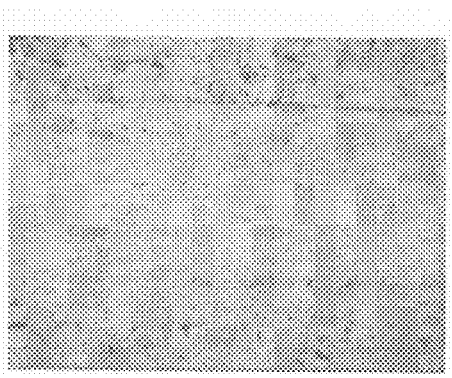
Fig. 22A                    Fig. 22B
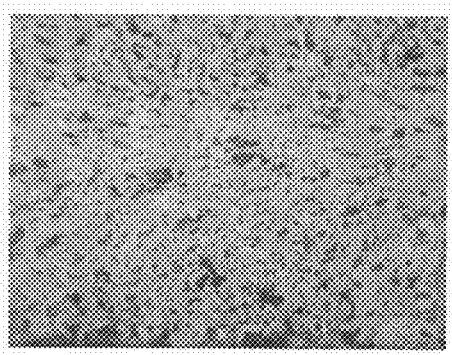
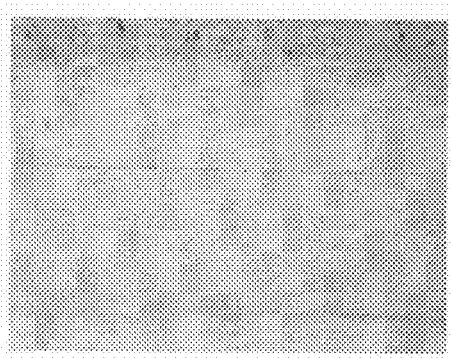
Fig. 23A                    Fig. 23B
Untreated                   SAW treated
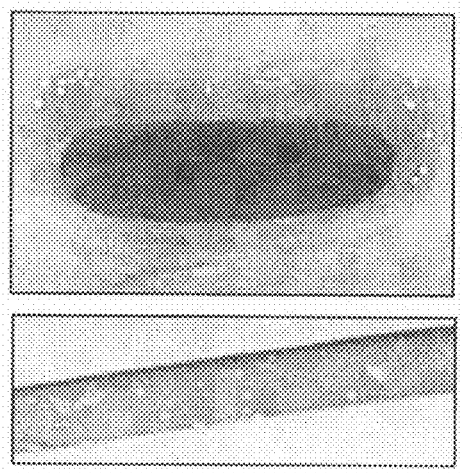
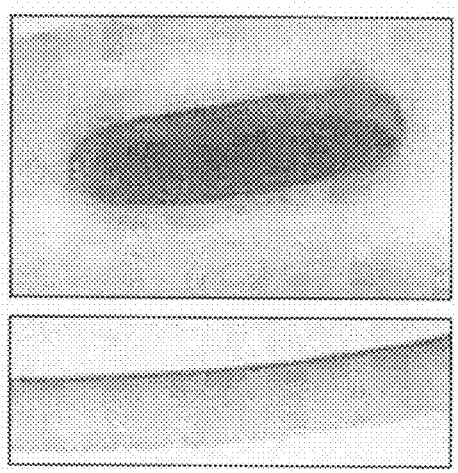
Fig. 24A                    Fig. 24B Control *Candida albicans*

SAW treated *Candida albicans*

Control *Pseudomonas aeruginos*

SAW treated *Pseudomonas aeruginos*

Control *Staphylococcus Aureus*

SAW treated *Staphylococcus Aureus*

ACOUSTIC ADD-ON DEVICE FOR BIOFILM PREVENTION IN URINARY CATHETER

CROSS REFERENCE TO RELATED APPLICATIONS

This application claims priority from U.S. Provisional Patent Application No. 60/786,701, filed Mar. 29, 2006, under 35 U.S.C. §119(e), and also from U.S. patent application Ser. No. 10/445,956, filed May 28, 2003, under 35 U.S.C. §120, which claimed priority from U.S. Provisional Patent Application No. 60/383,592, filed May 29, 2002, under 35 U.S.C. §119(e).

FIELD OF THE INVENTION

The invention relates primarily to the field of nanotechnology. More specifically, the invention pertains to a urinary catheter clip-on device for applying surface acoustic waves to a urinary catheter for preventing biofilms on the catheter surfaces.

BACKGROUND OF THE INVENTION

In-dwelling device related infections constitute a major cause of morbidity and mortality in hospitalized patients and add considerably to medical cost. Microbial biofilms tend to readily develop on all types of devices, urinary, endotracheal, intravenous, and implants inserted into more than 25% of patients during hospitalization. The incidence of bacterial infections in catheterized patients is approximately 5-10% per day with virtually all patients who undergo long-term catheterization ($\geq$28 days) becoming infected.

The first stage in biofilm formation from planktonic micro-organisms is adhesion to solid surfaces. Adhesion stimulates bacterial or fungal aggregation and proliferation forming micro-colonies. The colonies excrete an encasing exopolysaccharide 'slime' which consolidates their attachment to surfaces and the microaggregates differentiate into characteristic biofilms. Biofilm differentiation is also aided by quorum-sensing molecules which generate concentration gradient-dependent signals that control and alter the expression of a large number of genes.

The encasing extracellular polysaccharide matrix regulates the exchange of ions and nutrients between biofilms and their surrounding environment. This regulation contributes to approximately 1000 fold increase in the resistance of biofilms to antibiotics as compared with planktonic bacteria. Microbial biofilms also present serious challenges to the immune system because the expression of bacterial antigens within the encasing polysaccharide matrix is suppressed and the colony structures are highly resistant to phagocytosis. Altogether, these properties render biofilms exceedingly difficult to eradicate and explain the severity, persistence, and high levels of morbidity associated with infections produced by biofilms.

Current materials from which such medical devices are made include silicone rubber, Teflon®, polyethylene (PE), polypropylene (PP), polyvinyl chloride (PVC), polyurethane (PU), polytetrafluoroethylene (PTFE), Nylon®, polyethylene terephthalate (PET), and glass. These materials, however, lack the desired degree of slipperiness rendered by having a low coefficient of friction. It is necessary for the surface of these medical devices to have a low coefficient of friction to prevent injury, irritation, or inflammation to the patient and also to facilitate medical and surgical procedures.

Technologic innovations to prevent nosocomial infection are most likely to be most effective if they are based on a clear understanding of the pathogenesis and epidemiology of the infection. Novel technologies must be designed to block Catheter Associated Urinary Tract Infections (CAUTI) by either the extraluminal or intraluminal routes or both. Technologic innovations have been proposed and evaluated during the past 25 years but have not proven conclusively beneficial. Among these innovations are using anti-infective lubricants when inserting the catheter; soaking the catheter in an anti-infective, anti-microbial drug solution before insertion; continuously irrigating the catheterized bladder with an anti-infective solution through a triple-lumen catheter; or periodically instilling an anti-infective solution into the collection bag. Bladder irrigation with anti-microbial drug solutions has not only shown no benefit for prevention, but has been associated with a strikingly increased proportion of CAUTIs caused by microorganisms which are resistant to the drugs in the irrigating solution.

Given the widely accepted importance of closed catheter drainage, efforts have been made to seal the connection between the catheter and the collection tubing. An initial trial with a novel catheter showed a modest benefit and suggested a reduction in hospital deaths; however, follow-up studies have not demonstrated a reduction in CAUTI with a sealed catheter-collecting tube junction.

The severe and potentially fatal consequences of microbial biofilm infections have generated efforts to prevent biofilm formation, particularly on indwelling devices. Catheters coated with hydrogel, silver salts, and anti-microbials have been proposed, however they provide minimal reduction in infection incidence. A somewhat better efficacy appears to be achieved with releasable swiveling catheter securement devices.

Medicated catheters, which reduce the adherence of microorganisms to the catheter surface, may confer a greater benefit for preventing CAUTI. Two catheters which are impregnated with anti-infective solutions have been studied in randomized trials. One was impregnated with the urinary antiseptic nitrofurazone and the other with a new broad-spectrum anti-microbial drug combination, minocycline, and rifampin. Both catheters showed a significant reduction in bacterial CAUTIs; however, the studies were small, and selection of anti-microbial drug resistant uropathogens was not satisfactorily resolved.

The universal presence of a biofilm on the surface of an infected catheter has prompted hope that coating the catheter surface with an antiseptic, such as a silver compound, might reduce the risk for CAUTI. However, silver oxide-coated catheters, which had been initially reported to show promise, did not show efficacy when studied in large, well-controlled trials. In one of the trials, male patients who did not receive systemic antibiotics and had a coated catheter had a paradoxical and inexplicably increased risk for CAUTI.

Studies have shown that the addition of low-frequency ultrasound simultaneous with the application of antibiotics enhances the effectiveness of the antibiotic in killing the bacteria. In-vitro experiments to this effect were reported. It was found that when ultrasonic energy in conjunction with administration of an antibiotic (gentamicin) was applied to bacteria sequestered in a biofilm, a significantly greater fraction of the bacteria were killed than by using the antibiotic alone. Ultrasound by itself was not found to have any significant effect on the bacteria.

Similarly, it was found, that a synergistic effect was observed when ultrasound was applied in combination with gentamicin to in-vitro bacterial biofilms. These results may have application in the treatment of bacterial biofilm infections on implant devices. Ultrasound by itself was not found to be effective in inhibiting bacterial growth, except possibly at power levels high enough to cause cavitation. However, this would damage surrounding tissues in the body, as well.

Mechanical approaches to preventing biofilm formation have utilized ultrasonic energy, yet the focus has thus far been on increasing biofilm sensitivity to antibiotics. Ultrasound combinations with antibiotics were found effective only in reducing E. Coli biofilm burden in animal models, and fall short of providing a comprehensive solution to the biofilm problem.

The biofilm is formed due to intraluminal and extraluminal contamination (as shown in FIG. 1, routes of entry of uropathogens to catheterized urinary tract). Recent studies show that CAUTI most frequently stem from microorganisms gaining access extraluminally (66%) and intraluminally (34%). Extraluminal contamination may occur early, by direct inoculation when the catheter is inserted, or later, by organisms ascending from the perineum by capillary action in the thin mucous film contiguous to the external catheter surface. Intraluminal contamination occurs by reflux of microorganisms gaining access to the catheter lumen from failure of closed drainage or contamination of urine in the collection bag.

The aforementioned methods all aim to clean the medical device from contaminations and accumulated deposits, and not by fighting against the initial access of bacteria; not by pushing them out and not by preventing the first step of biofilm formation which is the adhesion of bacteria to a surface.

For example, U.S. Pat. No. 6,681,783 (Kawazoe) describes a method of cleaning a medical instrument which already has developed contamination on the inner side of the device by inserting an additional cleaning catheter with ultrasonic vibrators. (This may also be a biofilm.) A second cleaning device cleans the first one. The disadvantages of this method are:

1. The urinary or IV catheter cannot function during the cleaning procedure because the functional passageway will be used for inserting an additional cleaning catheter. This prevents the use of these types of catheters because, since they are disposable, they would not be cleaned.
2. Only the internal surface of the medical device could be cleaned with this method. This leaves the external surface (on which the most biofilm develops) without treatment.
3. As is known in the art, the ultrasound energy levels for cleaning purposes are very high which contradicts with safety requirements.
4. The device needs to be extremely small so that it may enter the channel of the catheter. Typically, the diameter of the internal channel of a urinary catheter is approximately 2 mm and the diameter of the internal channel of an IV catheter is approximately 1 mm. This prevents the use of these types of catheters. Using Kawazoe's transducer for urinary and IV catheters is therefore technically impossible.

U.S. Pat. No. 5,271,735 (Greenfeld) proposes to solve the cleaning of catheter external surfaces by making special grooves on the catheter surface. These grooves trap contaminating debris by transmitting energy through these grooves, thus disabling the microorganisms. Disadvantages of this device include:

1. This device could not be applied to a standard medical device because it needs to create a special construction catheter.
2. The formation of biofilm is not prevented.
3. Extraluminal and intraluminal bacteria access is not prevented.
4. Due to high energy levels being used, a special medical device must be constructed because the energy levels applied for cleaning are too high for safe and continuous use. These energy levels will change the mechanical qualities of the device and leaching problems will arise.
5. The energy levels which disintegrate bacteria, will, on the other hand, damage tissue in contact with the catheter.

U.S. Pat. No. 4,698,058 (Greenfeld) describes conveying vibrations to proximal orifices of the indwelling catheter for disintegrating accumulated deposits and contaminating bacteria in these specific places (orifices). This means that the problem is only overcome at specific places—to clean deposits on proximal orifices of the medical device. The vibration energy may be transmitted through fiber or liquid. The source of vibrations energy is a standard ultrasound transducer. Shear and compressional waves are applied. Disadvantages of this device include:

1. The transducer is a horn type which transfers the vibrations in one direction only—longitudinal. Such vibrations will push bacteria into the body, which is opposite to what is desired.
2. The beginning of the process, when the catheter is inserted into the urinary tract is a sterile system. If bacteria are prevented from entering, then the formation of a biofilm will be prevented. This will also solve the CAUTI problem.
3. Additional sensors are taught for sensing functions.

Clinical ultrasound systems are mainly used for imaging, although there are also some therapeutic devices in use and others that have been suggested in the patent literature. For example, Talish, in International Patent Application No. PCT/US98/07531, whose disclosure is incorporated herein by reference, describes an apparatus for ultrasonic bone treatment. The apparatus includes a therapeutic ultrasonic composite comprising a transducer and an integrated circuit unit positioned adjacent thereto. In operation, the apparatus is placed against the skin adjacent to a wound area, and driving signals are transmitted to the transducer for the creation of therapeutic ultrasound in the area of the bone. Another device of this type, for promoting vascularization and epitheliazation of a wound inside the body is described in U.S. Pat. No. 5,904,659 (Duarte et al.), whose disclosure is also incorporated herein by reference.

U.S. Pat. No. 5,725,494 (Brisken), whose disclosure is incorporated herein by reference, describes an ultrasonic catheter with a resonantly-vibrating assembly at its distal end for treating vascular clot and plaque. The distal end is positioned in the area of a clot or stenosis in a blood vessel, and the vibrating assembly administers ultrasonic energy to break up the clot or other stenotic lesions. The catheter may also be used in conjunction with a therapeutic agent.

U.S. Pat. No. 7,014,627 (Bierman), whose disclosure is incorporated herein by reference, deals with catheter securement system, and describes and claims the specific construction for catheter securement to the patient's body. Another relevant patent is U.S. Pat. No. 4,397,647 (Gordon), whose disclosure is incorporated herein by reference, which deals with constructions of catheter securement systems. Neither of these references contains active elements in the securement system like the one proposed in the invention.

A welcome addition to the art would be a medical device having the ability to prevent biofilm formation on surface areas of devices, as well as methods of increasing a level of such prevention in other medical devices.

SUMMARY OF THE INVENTION

According to one aspect of the invention, a clip-on device for preventing catheter associated urinary tract infections by creating surface acoustic waves that are distributed through energy transmission lines on the catheter is disclosed. Such infections typically occur by catheter contamination both extraluminally and intraluminally.

The device of the present invention disrupts the initial step in biofilm formation which is typically the attachment of bacteria to catheter surfaces. By generating acoustic waves, physical surface displacement hamper bacterial adhesion to the catheter surface by physically blocking bacterial attachment to the surfaces of the catheters. In this way, biofilm formation is prevented. Unattached bacteria are therefore more easily attacked by the local host immune mechanisms, since there is no longer any biofilm shielding the bacteria from the immune system. The device of the present invention also disrupts biofilm formation on catheters, by coating complex structures, such as urinary catheters, which vary in density and composition, with a corona of acoustic waves.

The bacteria are forced to move relatively the vibrating catheter surface. The relative motion of bacteria results in bacteria quorum sensing and disrupts the bacteria attachment process. The method is preventive as surface acoustic waves create low acoustic energy and bacteria are not killed.

The device comprises: an actuator coupled to an external part of a catheter or its accessories, outside of the body and a driver electrically connected there between. The actuator generates and transmits acoustic surface waves on and around the catheter (and/or its accessories) preferably in at least one of two directions: towards the patient's body and towards the urinary bag. These surface waves mechanically create relative velocity of bacteria in attitude to the catheter surface, and this relative velocity thereby preventing bacteria attachment to the catheter surfaces. The oscillations surround the catheter surfaces with a micro motion process of liquid and particles in an opposite direction to wave propagation direction.

In one embodiment, the surface acoustic waves are of Rayleigh-Lamb and/or Love type and generate an elliptical oscillation amplitudes of bacteria, which amplitudes are smaller than the Z potential repulsive zone. An overall net repulsion therefore occurs, which is effective in inhibiting bacterial attachment to urinary catheter surfaces, inhibiting the adhesion, growth, and aggregation of cells into microcolonies on the urinary catheter surfaces, and inhibiting the maturation and dissemination of progeny cells for new colony formation.

In one embodiment, an actuator is attached to a standard medical device (from the outside of the body, to an inner surface of the catheter) and generates directional vibrations on the surfaces of the standard medical device. These vibrations prevent the formation of extraluminal and intraluminal bacteria access into the sterile system. Unlike the teachings of Kawazoe and Greenfeld the construction of the medical devices themselves are unchanged. Major advantages of the present invention include:

1. Preventing bacterial adhesion to the surface due to the interruption of the first stage of biofilm formation.
2. Creating vibrations directed for preventing intraluminal and extraluminal bacteria access by pushing them out of the body, thereby preventing the occurrence of the problem.
3. Never closing the functional passageway of the catheter with an additional cleaning apparatus. In this way, the device functions all the time.
4. Experiments have demonstrated that the energy levels for preventing bacterial growth are much lower (more than $10^3$ times) than for cleaning tasks. Thus the use of the present device increases safety.

The mechanical amplitudes of the surface acoustic waves of Rayleigh-Lamb and/or Love type are in the range from about 0.1 to about 5 nanometers. The frequency ranges from about 100 KHz to about 1 MHz. The waves are of running wave type. The velocity of the running wave ranges from about 14 to about 30 m/s. The magnitude is close to the acoustic wave velocity in the skin. The acoustic waves do not irritate the tissue.

The actuator created vibrations lower the connection time between tissue and catheter, thereby influencing friction and preventing injury, irritation and inflammation, insuring less pain and less trauma to the patient and facilitating medical and surgical procedures.

The actuator in patch configuration solves the above mentioned problems and in addition secures the catheter system to a patient's leg, thus inhibiting mechanical trauma.

Additional objects will be apparent from the following description.

BRIEF DESCRIPTION OF THE DRAWINGS

A specific embodiment of the present invention is described with reference to the following drawings, wherein:

FIG. 3 is a schematic illustration of an acoustic system with piezo element 110, according to some embodiments of the present invention, for preventing or treating the formation of microbe colonies on a catheter and directing acoustic waves.

FIG. 12B shows a double side paper sticker having a small tongue glued to a piezo element.

FIGS. 22A, 22B, 23A, and 23B are views of an experimental result in biofilms in activated lines and a control group.

FIGS. 24A and 24B shows that surface acoustic waves caused marked reductions in biofilm formation on the surface of activated catheters as compared with controls.

DETAILED DESCRIPTION OF THE INVENTION

Figure 1:
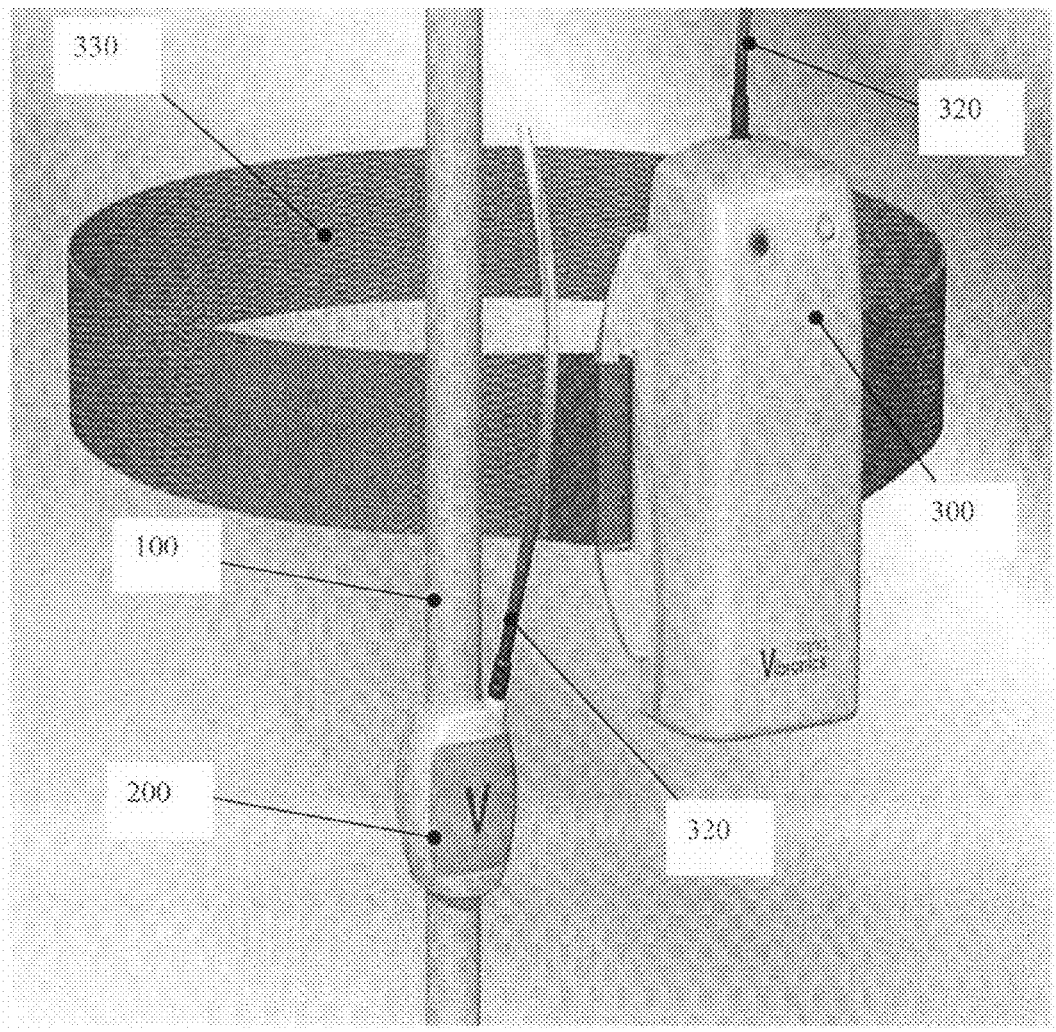
FIG. 1 is a schematic illustration of the system of the present invention.

The following preferred embodiment of the invention is illustrative of the invention and is not intended to limit the invention as encompassed by the claims of this application. Various modifications to the described embodiments will be apparent to those skilled in the art and the general principles defined herein may be applied to other embodiments. Well-known methods, procedures, and components, have not been described in detail so as not to obscure the present invention.

The word "biofilm" as used herein may encompass microbes, microorganisms, viruses, fungi, deposits, particles, pathogenic organisms, cells, and other bioactive materials. The word "pathogenic microorganisms" as used herein may encompass any organisms, including bacterium or protozoan. Such organisms may be harmful, infectious, or non-harmful.

According to an embodiment of the present invention, an acoustic apparatus is provided, which may prevent or treat the formation of microbe colonies. These microbe colonies may lead to the development of harmful biofilm(s), which may include various pathogenic microorganisms or infections. The acoustic apparatus may comprise at least one piezo-ceramic element and a vibration processing unit that, when attached to a standard catheter, may produce vibrations, for example micro-vibrations, that may disperse microbe colonies. The piezo-ceramic element may be attached to any conventional catheter such as, for example, a gastrostomy catheter, cardiovascular catheter, lung catheter, urinary catheter, etc. Any other catheters may be used. A processor, such as a vibration processor, may supply electric signals, which may be transformed by the piezo-ceramic element(s) into mechanical vibrations, such as sound waves. The vibrations may cause the piezo-ceramic element to oscillate, thereby creating vibrations on the catheter surfaces and/or partially propagating to the relevant internal organs, cavities, passageways etc.

According to an embodiment of the present invention, the vibrations, which may be micro-vibrations, may be significantly amplified if a resonance condition is attained in the catheter, balloon, and/or internal area. A resonance condition may cause an increase in the amplitude of oscillation of the acoustic apparatus when exposed to a periodic force whose frequency is equal to or very close to the natural undamped frequency of the apparatus. This resonance may intensify and/or prolong the acoustic vibrations generated by the piezo-ceramic element(s), relative to the energy supplied by the vibration processor. The effects of resonance may further aid in the dispersal of microbe colonies that have grouped around the catheter and/or the inner organs or of microbe colonies that are attempting to do so.

The PZT element may be tightly attached to an inner or outer catheter surface, and, as a result of this attachment, vibrations from the ceramic elements (thickness, longitudinal, torsion, flexural (bending)-flexural, longitudinal (radial)-flexural, radial-longitudinal, flexural (bending)-torsional, longitudinal-torsional and radial-shear modes) may be transmitted through the catheter material, through inner catheter surfaces and/or through outer catheter surfaces, generating traveling surface acoustic waves, e.g., of Rayleigh-Lamb type and/or Love type. The frequency and amplitudes of PZT element vibrations are adjusted to catheter shape and material to enable creation of surface acoustic waves on inner and outer surfaces of the device along its entire length. Furthermore, the acoustic energy which is transmitted through catheter surface is adjusted to create mechanical micro-vibrations capable of preventing biofilm formation on the catheter surface and/or dispersing or disrupting biofilm formation.

The energy of micro vibrations is adjusted so as to force the bacteria to move relative the vibrating catheter surface. The relative motion of bacteria in relation to the catheter surface results in disruption of the bacteria attachment process and influence on other biofilm formation process components, such as bacteria quorun sensing. The relative motion of bacteria may be created with low acoustic energy, such that the proposed method does not employ energies in the bacteria-killing range. The proposed method is preventive distribution of low acoustic energy by means of surface acoustic waves for inhibiting bacteria attachment to surfaces, and this principle differs from known bacteria killing methods using high energy.

The proposed device has a thin plate piezo actuator, which, after activation by a processor, begins to vibrate in bending vibration modes, creating standing waves on the PZT plate. Multiple energy picks interchange with minimal energy levels on the actuator surface and act like small energy needles. Due to these energy picks, "energy needles" actuator creates surface acoustic waves on the catheter surface, which in the form of running waves are transmitted along its entire length. In addition, the thin plate actuator creates acoustic waves in the inner catheter channels.

The term "surface acoustic waves" or "SAW" as used throughout the present disclosure, includes several types of waves or combinations thereof, as follows: surface: Rayleigh (elliptical orbit—symmetrical mode), plate wave: Lamb—component perpendicular to surface (extensional wave), plate wave: Love—parallel to plane layer, perpendicular to wave direction, Stoneley (Leaky Rayleigh Waves); wave guided along interface, and Sezawa: antisymmetric mode. Surface or Rayleigh waves travel along the boundary between two different media, penetrating to a depth of about one wavelength. The particle movement has an elliptical orbit. Lamb wave is a special case of Rayleigh waves, which occurs when the material is relatively thin. The physical motion of surface acoustic wave of Rayleigh-Lamb and/or Love type is associated with mechanically time-dependent elliptical displacement of the surface structure.

One end of the catheter may have a form of or include a balloon. The frequency and modes of vibrations in piezo-elements (separately or in combination) may be chosen in such a way so as to achieve vibration resonance of the balloon volume. As a result, the balloon itself may become a source of vibrations. These vibrations may be transmitted in different directions, for example, in the direction of the body, in the longitudinal direction of the catheter (through its inner/outer surfaces), away from the body etc.

The frequency of transmitted waves may depend on the catheter type or on the construction (for example, the material, manufacturing, etc.) and may not be the same as piezo-ceramic resonance frequency. By means of a processor, in addition to choosing the proper resonance frequency of piezo-ceramic elements, it may be possible to achieve effective vibrations on the surface of a catheter.

The vibrations from piezo-elements and catheter surfaces may be transmitted to the liquids or materials that are in contact with the piezo-elements. These liquids and materials may receive micro vibration energy, thereby preventing the formation of biofilm.

The above mentioned combinations of vibration modes may be necessary because the various catheters that are available in the market are made of different materials and are manufactured in different resolutions, and because every patient has different biofilm microbiology. In order to get the desired result, a particular combination of vibration modes may need to be applied for each patient. Additionally, in order to generate resonance vibrations in the balloon, a particular combination of vibration modes may need to be applied for each balloon. Since different balloons have different volumes and may be made of different materials etc., the outer loading of each balloon may differ. It may, therefore, be necessary to apply different combinations of vibration modes, in order to generate a mode that is similar to the natural vibration mode of the balloon, such that resonance of the balloon vibration may be achieved.

The vibrating of the balloon may act as an additional piezo-element on the inner end of the catheter. The direction of the vibrations caused by the balloon may be different than or opposite to the direction of the surface vibrations, caused by piezo-elements. In this way, biofilms may be transferred out of the body together with exiting liquids.

The present invention includes an innovative approach in which ultrasonic energy is transmitted directly to urinary catheter surfaces by applying an add-on miniature device. High frequency acoustic waves are generated from electrically activated piezoceramic elements for homogeneously dispersing on surfaces of indwelling medical devices which may vary in consistency and shape. The medical devices act as lines of acoustic mechanical energy transmission. To achieve the effective physical energy requirements for harnessing these waves for preventing microbial attachment and biofilm formation, piezo-actuators generating high frequency elastic acoustic waves of non-thermal range applied to a wide range of microorganisms on indwelling medical devices in vitro and in animal models are presented.

High frequency low energy "elastic waves" generated from electrically activated piezo-ceramic elements which are designed to travel on solid or semi-solid surfaces, effectively prevent formation of microbial biofilms on solid surfaces of variable structures. The development of biofilms by ten different bacteria and Candida species have been prevented by applying high frequency elastic waves with nanometer range amplitudes. The propagation of the elastic waves can be adjusted to distribute evenly on inert surfaces with different compositions and materials bearing multiple shapes including tubing structures. Internal, external, and cross-sectional zones may be covered with elastic waves. In addition to longitudinal dispersion, these may acquire a transversal vector surrounding the surface with a corona of waves perpendicular to the surface of dispersion. The acoustic elastic wave corona is repulsive to bacteria and interferes with their docking and attachment to solid surfaces, which constitutes the initial phases of microbial biofilm development.

For example, in one example, minute piezo-actuators generating acoustic waves onto 8 Fr or 10 Fr urinary catheters have been inserted into the meatus of male rabbits. Urine sterility in nanowave-treated inserted catheters was attained up to $\leqq 9$ days as compared with 2 days in control animals. Scanning electron microscopy revealed reduced microbial biofilm formation on the surfaces of these catheters.

The ability to coat complex structures such as urinary catheters, which vary in shape, density and composition (for example, a rigid eyelet and a flexible balloon), with a corona of acoustic waves that prevent microbial biofilm formation can potentially be adapted to different indwelling catheters, for example, endotracheal tubes, central venous or peritoneal dialysis catheters, as well as to other medical devices. The entire indwelling medical device industry (including mechanical heart valves, pacemakers, prosthetic joints, and others), could potentially benefit from this approach.

In a first aspect of the invention, a medical device is disclosed comprising an actuator for providing surface acoustic waves. The actuator may comprise a thin piezo-resonator. This excites a virtual nano-coating process, having vibration amplitudes ranging from about 0.2 to about 2 nanometers.

According to some embodiments of the present invention, by means of applying combinations of mechanical vibrations and other various propagation techniques, nano-vibrations of very small amplitude and pressure are created on internal, external and/or torsional surfaces of a medical device. This represents a novel antibacterial coating, a "nano-vibration coating". The magnitude of the nano-vibrations is several times smaller, and can be up to ten times smaller, in comparison to the size of bacteria. Such small vibrations do not increase temperature. It is possible to control the magnitude, direction, and the rate of nano-vibrations on external and internal surfaces of a medical device. It is now possible propagate elastic waves of different types (different harmonics and directions) simultaneously. This creates spacious nano-elastic waves on internal, external, and torsional surfaces of a medical device.

Other features that are created by the surface vibrations of the antibacterial coating of nano-vibrations may include: a decreased bacteria violence, a greater durability, and many other abilities, including repair of an aneurysm, creating an anastamosis, resisting the crystallization of body fluids, resisting the formation of thrombus, resisting tissue in-growth, enabling better drug administration, adhesion, non-adhesion, friction, patency, or anti-biofouling.

Current materials from which catheters are made include silicone rubber, Teflon®, polyethylene (PE), polypropylene (PP), polyvinyl chloride (PVC), polyurethane (PU), polytetrafluoroethylene (PTFE), Nylon®, polyethylene terephthalate (PET), and glass. These materials, however, lack the desired degree of slipperiness. Surface acoustic waves the decrease time of contact between tissue and catheter material and thus—may influence the friction and prevent injury, irritation, or inflammation to the patient. This will facilitate medical and surgical procedures. Furthermore, the same effects will be achieved for catheters manufactured from materials having enhanced surface area substrates, such as nanofiber substrates and other riffled surfaces.

Reference is now made to FIG. 1, which is a schematic illustration of the system of the present invention. The inventive system is designed as a low cost, disposable device that is attached to the extracorporeal portion of a conventional urinary catheter 100. The system comprises an actuator 200 and a driver 300 that are electrically connected by cable 320. The driver 300 may be attached to the belt 330, which may be further attached to a patient's back, leg, bed, urinary bag, etc.

The actuator generates an acoustic surface wave on the catheter and/or accessories and transmits these acoustic surface waves around the catheter surfaces in at least one of a direction towards the patient body and a direction towards urinary bag. These surface waves mechanically create an oscillation and relative velocity of bacteria in attitude to the catheter surface. This prevents bacterial attachment to the catheter surfaces and creates a surface micro motion process of liquid and particles which surrounds the catheter in a direction opposite to the direction of surface acoustic wave propagation.

As previously described, the device of the present invention may be used as an accessory to urology catheters and may have either—antibiotic based or a silver based coating for disrupting biofilm formation on catheters. The system disturbs the initial step in biofilm formation, which is bacterial attachment to the surfaces of the catheter. This is accomplished by creating low-energy surface acoustic nano-waves at average amplitudes of about 2 nanometers, with a frequency range of from about 0.1 to about 2 MHz. These surface acoustic waves result in physical surface displacement motions of the catheters. These motions hamper bacterial adhesion to the catheter surface by physically blocking bacterial attachment to the surfaces of the catheters. In this way, the biofilm forming cascade can be interrupted. The resultant unattached bacteria are then more easily attacked by the local host immune mechanisms, since there is no biofilm to shield the bacteria from the immune system. In the case of the presence of an antibiotic, silver or any other catheter anti-microbial layer, the effective life of such layers is lengthened because they remain clean from conditioning layer.

A resonator of the actuator uses a thin PZT plate element. Periodic rectangular electrical pulses are applied. The thin PZT plate element begins mechanical vibrations in a normal mode, when the distance between nodal points is proportional to the acoustic wavelengths. Since the attenuation between the urinary catheter surface and the air is very low, all acoustic energy is transmitted to the indwelling part of the catheter. This part of the catheter is surrounded by fluids and tissues, and, therefore, at this location attenuation is far higher. As a result, the acoustic energy in this part of the catheter is derived at an angle, depending on the characteristics of the surrounding fluid and tissue. A part of energy continues as running SAW along the catheter length, another part which is known as a compression (transverse) wave, is the residual energy transmitted to the tissues.

It should be stressed, that this residual energy is a small fraction of the energy originating from the actuator. This is due to the following: half of the energy is transmitted in the direction of the urinary bag, and is distributed between outer and inner surfaces. The other half is transmitted towards the body, where again, it is divided in two parts: one part goes to the internal surface of the catheter (which is not in the contact with body tissues), and the remaining part is again divided.

Figure 2:
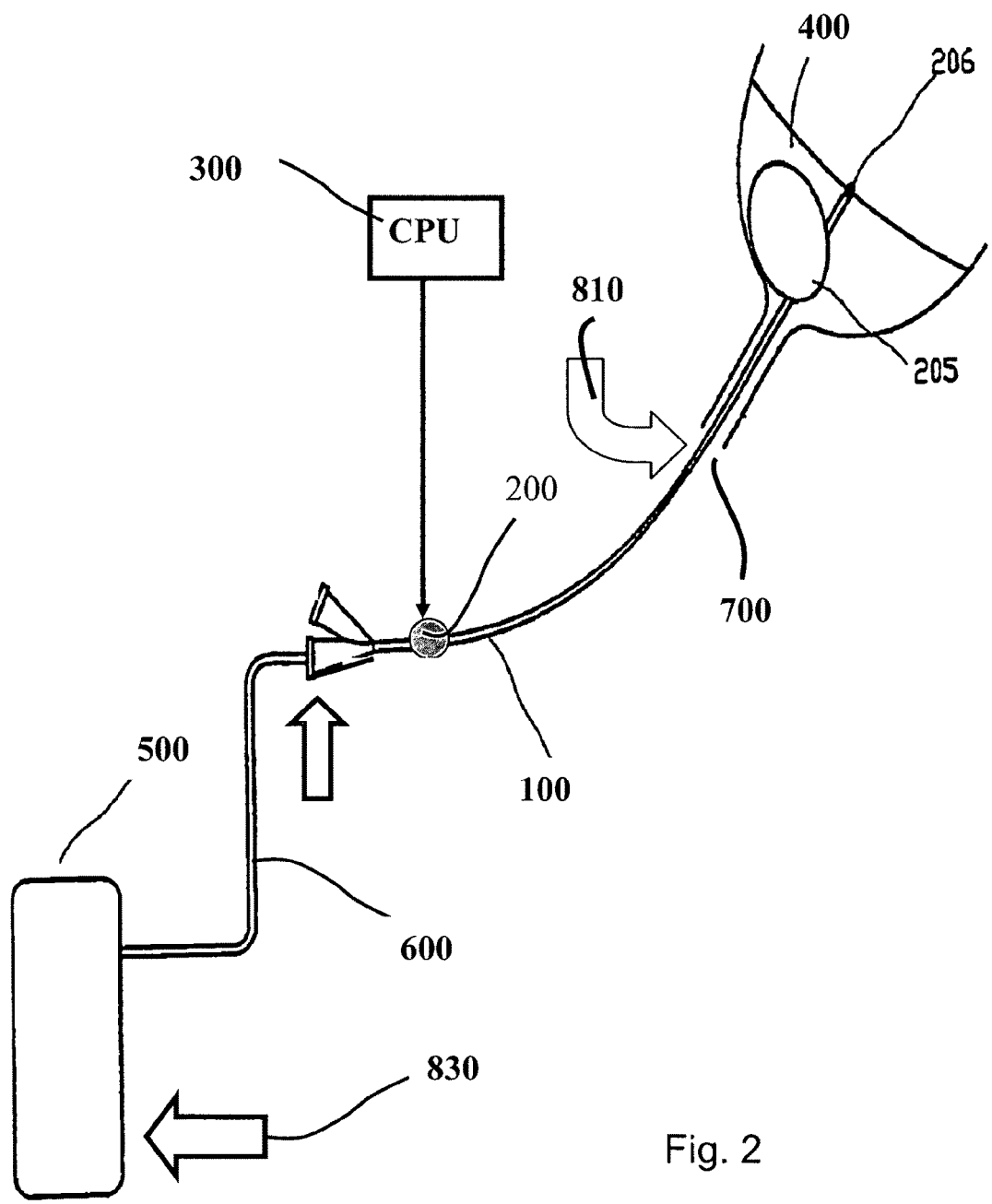
FIG. 2 illustrates a schematic view of the present invention applied to a catheter and routes of entry of uropathogens to a catheterized urinary tract.

Reference is now made to FIG. 2, which schematically illustrates routes of entry of uropathogens to catheterized urinary tract and an actuator 200 applied to this system. The indwelling urinary catheter 100 drains urine from a bladder 400 into a bag 500 through the catheter 100 and a bag drainage tube 600. The catheter is placed into the urethra through an orifice 700 and continues into the bladder. The actuator 200 is shown as being clipped onto the catheter 100 and connected to a driver (microprocessor) 300.

The formation of a biofilm begins by intraluminal and/or extraluminal contamination. Such contaminations respectively enter through extraluminal 810 and intraluminal 820, 830 entries. The extraluminal 810 contamination may occur early by direct inoculation when the catheter is inserted, or later, by organisms ascending from the perineum by capillary action in the thin mucous film contiguous to the external catheter surface. An intraluminal contamination may occur by the reflux of microorganisms gaining access to the catheter lumen from the failure of a closed drainage 820 or from contamination by urine 830 in the collection bag 500. Recent studies show that CAUTI most frequently stem from microorganisms gaining access extraluminally (66%) and intraluminally (34%).

Reference is now made to FIG. 3, which is a schematic illustration of an acoustic system with a piezo-element 210 connected with a driver (microprocessor) 300, according to some embodiments of the present invention, for preventing or treating the formation of microbe colonies on a catheter 100. The driver 300 transmits and controls electric signal to the actuator 200. The piezo-element 210 of the actuator 200 converts electrical signal to mechanical energy proportionally by range and time. As a result, piezo-element 210 begins to vibrate and conducts surface acoustic waves on an external 110, an internal 120 and end 130 surfaces of the catheter. The external 110 catheter surface may be understood to act as a vibration transmission line. The vibrations are transmitted in two directions: direction 910 towards the urinary bladder and direction 920 towards the urinary bag, and around the catheter in directions 930 and 940. Furthermore, the vibrations are partially transmitted through catheter material volume to the internal catheter surfaces 120.

The driver 300 is an external micro processing unit that is electrically connected to the piezo-element 210. The driver unit 300 contains a power system 301, a battery block 302, and a fault alarm system 303. The power system 301 comprises a generator, a DC/DC converter, and a driver system. The driver comprises a power indicator 304 (for example, green LED), a low battery circuit 305, a low voltage circuit alarm visual indicator 306 (for example, red LED), and an acoustic indicator 307 (buzzer). If the actuator 200 is disconnected from the driver, an indicator 308 (for example, yellow LED) and the buzzer 307 indicate the fault.

The driver supplies electric signals to the piezo-element, the signals being selected from at least one of the group or combinations thereof, comprising megahertz frequency signals, kilohertz frequency signals, and electric signals forms and duty cycles. The driver may be small enough to be integrated into the actuator 200 as a chip.

Figure 4:
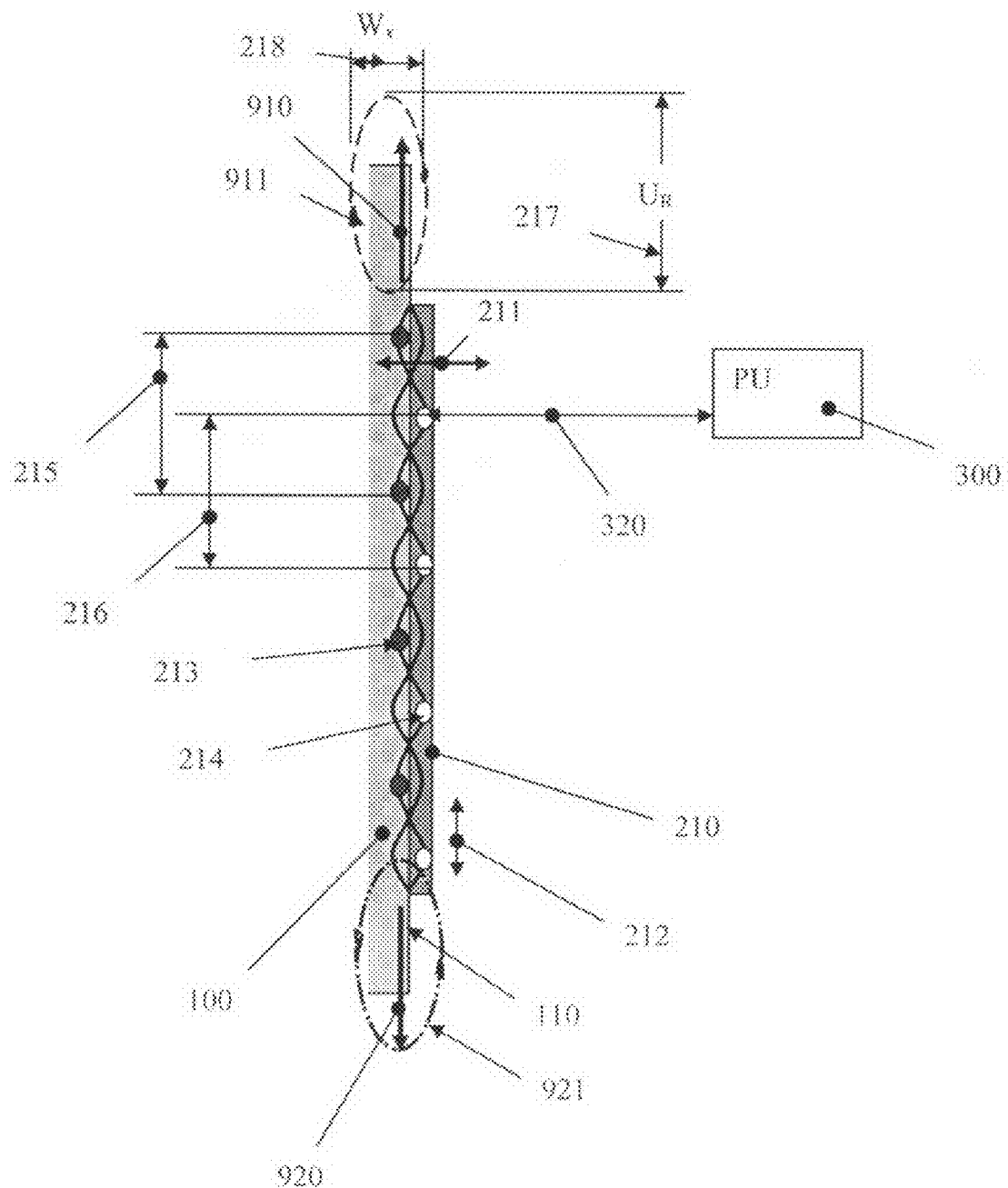
FIG. 4 is a schematic illustration of surface acoustic waves (SAW) generated on a urinary catheter surface.

Reference is now made to FIG. 4, which is a schematic illustration of surface acoustic wave (SAW) generation on a urinary catheter surface by the thin PZT plate element 210 which acts as a surface wave resonator. A periodic electrical pulse from the driver is applied to the thin PZT plate element, which begins producing mechanical vibrations in normal modes.

The piezo-element 210 is attached to the urinary catheter external surface 120, and is connected via the cable 320 to the power unit 300. The electrical signal excites piezo-resonator bidirectional vibrations 211 and 212 vibrations, which together is a bending vibration mode, depicted by the sinusoidal line with maximum 213 and 214 points. These max points 213 and 214 represent the mechanical vibration of the catheter surface 110.

The distance 215 between the points 213 is chosen so that it is approximately equal to half of the SAW length excited in the catheter material. Similarly, the distance 216 between the points 214 will be approximately equal to half of the SAW length excited in the catheter material. In this way, the running wave is excited on the surface of the catheter in the directions 910 and 920. These low-energy SAW waves fade with depth. Also, their physical motion causes time-dependent elliptical displacements 911 and 921 of the catheter surface components, as shown in FIG. 4. One longitudinal vector spreads parallel to the wave propagation along the x-axis, which is the surface of the catheter, triggering horizontal surface particle displacement ($U_R$) 217. The length of the surface wave $U_R$ is equal to the two distances 215 or 216 of the piezo-ceramic vibration. Another transverse compression wave component ($W_R$) 218 develops on the y-axis normal to the catheter surface causing displacement in the direction of the surrounding tissues or fluid. The amplitude of this wave $W_R$ is shown as distance 218. SAW excited on the catheter which have the direction of the propagating wave as shown as directions 910 and 920 and may be assumed to be Rayleigh type waves. Rayleigh type acoustic waves cause catheter surface particle oscillations in directions that are parallel to the wave propagation x-axis ($U_R$) along the surface and normal to the surface y-axis ($W_R$) triggered by Rayleigh waves. A calculation of the velocity and the amplitudes is as follows:

$$U_R = Ak_R\left(1 - \frac{2q_R S_R}{k_R^2 + S_R^2}\right)\sin(k_R x - ?t)$$

$$W_R = Aq_R\left(1 - \frac{2k_R^2}{k_R^2 + S_R^2}\right)\cos(k_R x - ?t)$$

where $q_R^2$, $S_R^2$, and A are constants calculated as follows: $q_R^2 = k_R^2 - k_t^2$ and $S_R^2 = k_R^2 - k_e^2$, and $k_R$ denotes Rayleigh wave numbers on the surface, $k_e$ and $k_t$ are the numbers of longitudinal and transversal waves respectively, $k_e = 2?f/c_e$ and $k_t = 2?f/c_t$ ($c_t$ being the longitudinal and $c_e$ the transversal acoustic velocities). In addition, $k_R = k_t/?_R$ and $?_R = (0.87 + 1.12?)/(1+\sigma)$, where ??? Is the Poisson ratio.

The parameters that define the surface acoustic waves used herein for preventing microbial biofilm development are: peak max particle displacement motion ($W_R$) of catheter surface components excited on the x-axis with elastic waves at a frequency of 100 kHz is 2 nm. $U_R$ calculated on the y-axis from formulas provided above, equals 3.73 nm. The velocity of surface point movement is $V_x=0.0023$ m/sec, the corresponding acceleration $a_x=1472.2$ m/sec$^2$, the y-axis velocity $V_y=0.0013$ m/sec and the acceleration $a_y=789.6$ m/sec$^2$. The velocity of Rayleigh acoustic waves was $C_r=28.324$ m/sec.

When the surface acoustic waves-generated bacterial relative elliptical oscillation amplitudes are smaller than the Z potential repulsive zone, an overall net repulsion occurs. This is effective in inhibiting bacteria attachment to urinary catheter surfaces, inhibiting adhesion, growth, and aggregation of cells into micro-colonies process on urinary catheter surfaces, and preventing maturation and dissemination of progeny cells for new colony formation.

In certain embodiments, the mechanical amplitudes of surface acoustic waves are in the range of from about 0.1 to about 5 nanometers. In certain embodiments, the frequencies range from about 100 KHz to about 1 MHz, and the waves are typically a running wave type. In certain embodiments, the velocity of the running wave ranges from about 14 to about 30 m/s, and the magnitude is close to an acoustic wave velocity in the skin. Additionally, the acoustic wave does not irritate the tissue.

The particles and bacteria on the catheter surface are forced into a direction opposite to the vibration transmission direction, thereby preventing extraluminal bacteria gain and forcing the bacteria out of the body.

These waves propagate in two directions 910 and 920: towards the urinary bag 500 and towards the human body 400. Consequently, the external surfaces of the catheter are covered with a virtual nano-vibrating coat. The urinary catheters have an inflation channel and stabilizing balloon, which are filed with compressed liquid. It is among the objectives of the device of the present invention to also excite the vibrations on the stabilizing balloon, and by causing the resonance of the balloon vibrations, to achieve an additional vibration source amplifying the excited vibrations.

Figure 5:
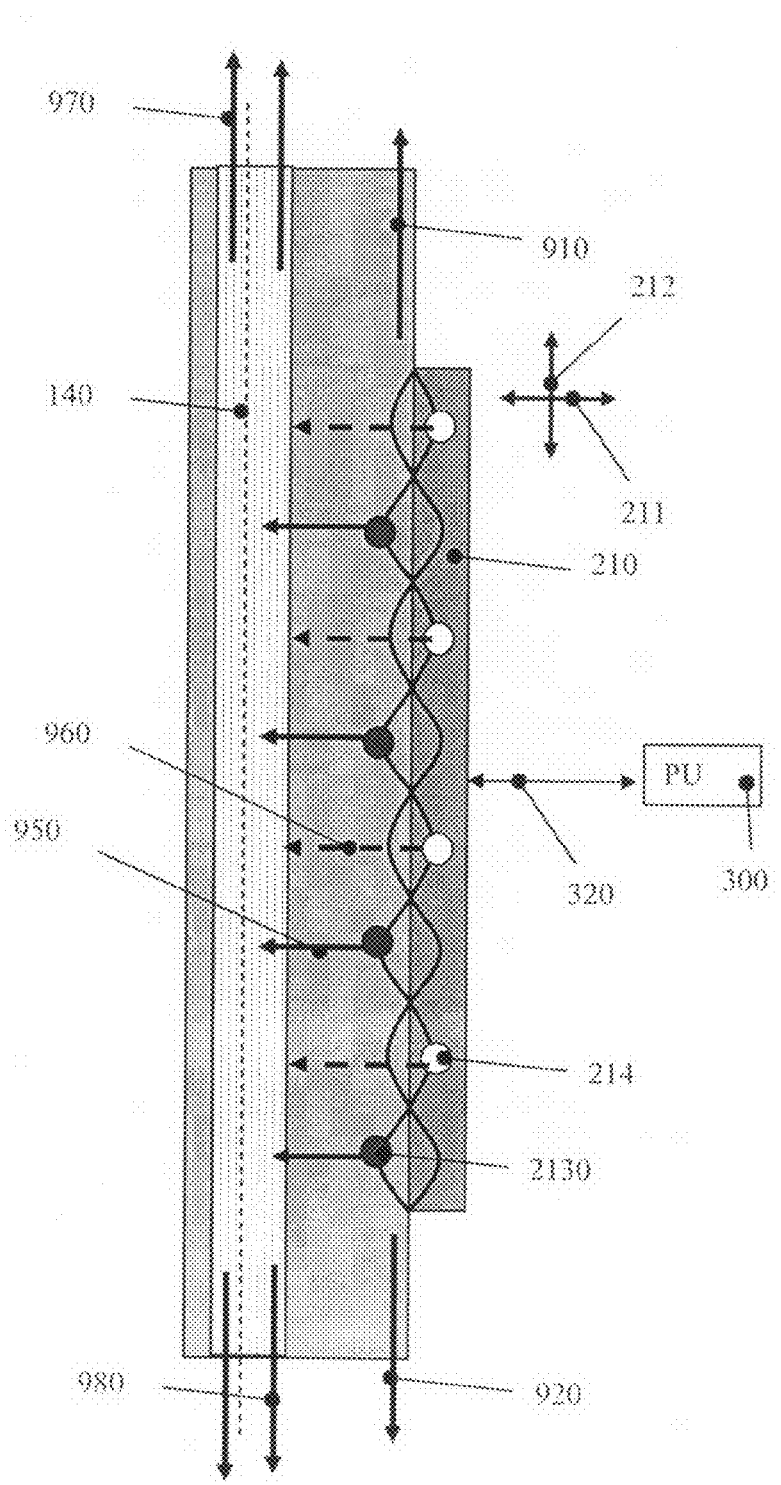
FIG. 5 is a schematic illustration of propagating vibration waves on the inflation channel of a urinary catheter.

Reference is now made to FIG. 5, which is a schematic illustration of vibration wave propagation towards the inflation channel 140 of the urinary catheter 100. The max amplitudes 213 and 214 of the piezo-element 110 (vibrating in a bending mode) excite not only SAW propagating in two directions 920 and 910, but also the compression vibration waves 950 and 960 propagating through the catheter material towards the inflation channel 140. These vibrations cause pressure changes of the liquid in the inflation channel, transmitting the vibration energy in two directions: towards the stabilizing balloon (see arrow 970) and in an approximately opposite direction (see arrow 980). As a result of the liquid pressures changes in the inflation channel and in the stabilizing balloon, they begin to vibrate. When the piezo-element bending vibrations frequencies are proportional to balloon self vibrations, the result will cause stabilizing balloon resonant vibrations. This results in spherical acoustic waves transmitting from the stabilizing balloon.

Figure 6:
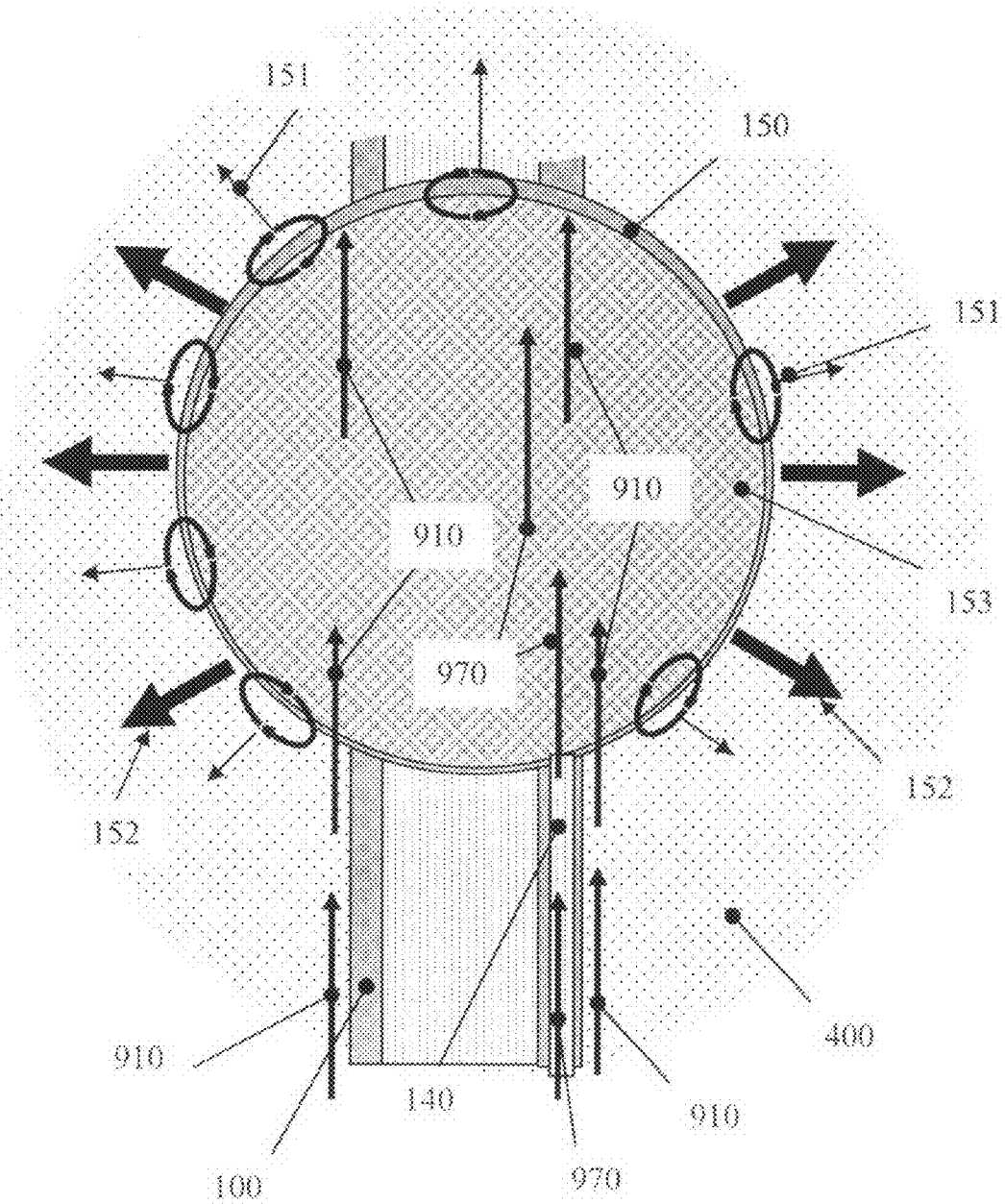
FIG. 6 is a schematic illustration of transmitting two wave types of acoustic energy, SAW and spherical acoustic waves, propagated from a stabilizing balloon surface.

Reference is now made to FIG. 6, which is a schematic illustration of acoustic energy transmission due to two wave types propagating from stabilizing balloon 150 surface: SAW 151 and spherical acoustic waves 152. The first wave type of transmission from the stabilizing balloon 150 surface is seen as SAW waves propagating in the direction 910 on the device surface 110 (as previously described, see FIG. 4.)

Spherical acoustic waves 152 are excited in the following manner. When the inflation channel 140 of the catheter 100 and the balloon 150 are filled with liquid, high frequency pulsating pressure is created. This pressure is created due to the actuator 200 action. The acoustic energy which is created in the inflation channel 140 is transmitted in the direction 970 towards the liquid filled the balloon 150. The frequency of the pulsating pressure is adjusted so as to cause the balloon 150 filled with liquid 153 to vibrate mechanically in self resonance. The balloon 150 starts to act as an energy condenser. This means that it conducts the energy transmitted through the inflation channel in small portions. In this way, the self resonance of the balloon vibrations is achieved. The amplitude of the vibrations of the balloon surface is 10 orders higher than the amplitude of vibrations of the inflation channel 140 surface. As a result, two wave types propagate from the stabilizing balloon 150 surface: SAW 151 and spherical acoustic waves 152.

The resonance of the balloon may depend on constant and/or variable parameters. In the case when a combination of vibrations is applied, one of the modes may correspond to the natural balloon self-vibration, causing it to vibrate in resonance. The urinary catheter balloon, which -is filled with water, acts similar to a Helmholtz resonator. This is defined by the weight and elasticity of the internal volume of the resonator's liquid.

Therefore, the balloon acts as an additional vibration source and transmits an acoustic spherical waves towards the patient's tissues. The acoustic energy may speed the rate of healing and enhance the quality of the repair due to acoustic streaming. Micromassage, a mechanical effect of acoustic energy traveling through the medium, may cause the molecules to vibrate, possibly enhancing tissue fluid interchange and affecting tissue mobility. The above effects will probably influence the general state of the patient's tissues and enhance healing processes in post surgery patients.

Thus, due to an additional vibration energy source from the balloon surfaces (stabilizing or therapeutical balloon), maximal vibrations may be achieved when actuator 200 is coupled to the catheter in a minimal distance from balloon inflation channel. The balloon vibrations are excited due to longitudinal type waves transmitted through liquids filling the inflation channel. The excited balloon resonance results from actuator oscillations in the same frequency as the natural balloon self resonance frequency. The balloon generated acoustic energy exceeds 5-10 times the surface acoustic energy excited on the catheter surface by the device, and the ranges of balloon mechanical vibration amplitudes are about 0.5-about 5.0 nm. The part of acoustic energy has a transversal vector of up to about 5 cm and thereby biofilm formation is prevented not only on the catheter surface but also on human tissue in adjacent contact with the catheter. By controlling the balloon pressure and shape, directional and focused acoustic energy from the balloon to body tissues in contact with it may be obtained, and controlled therapeutic effect may be applied.

Figure 7:
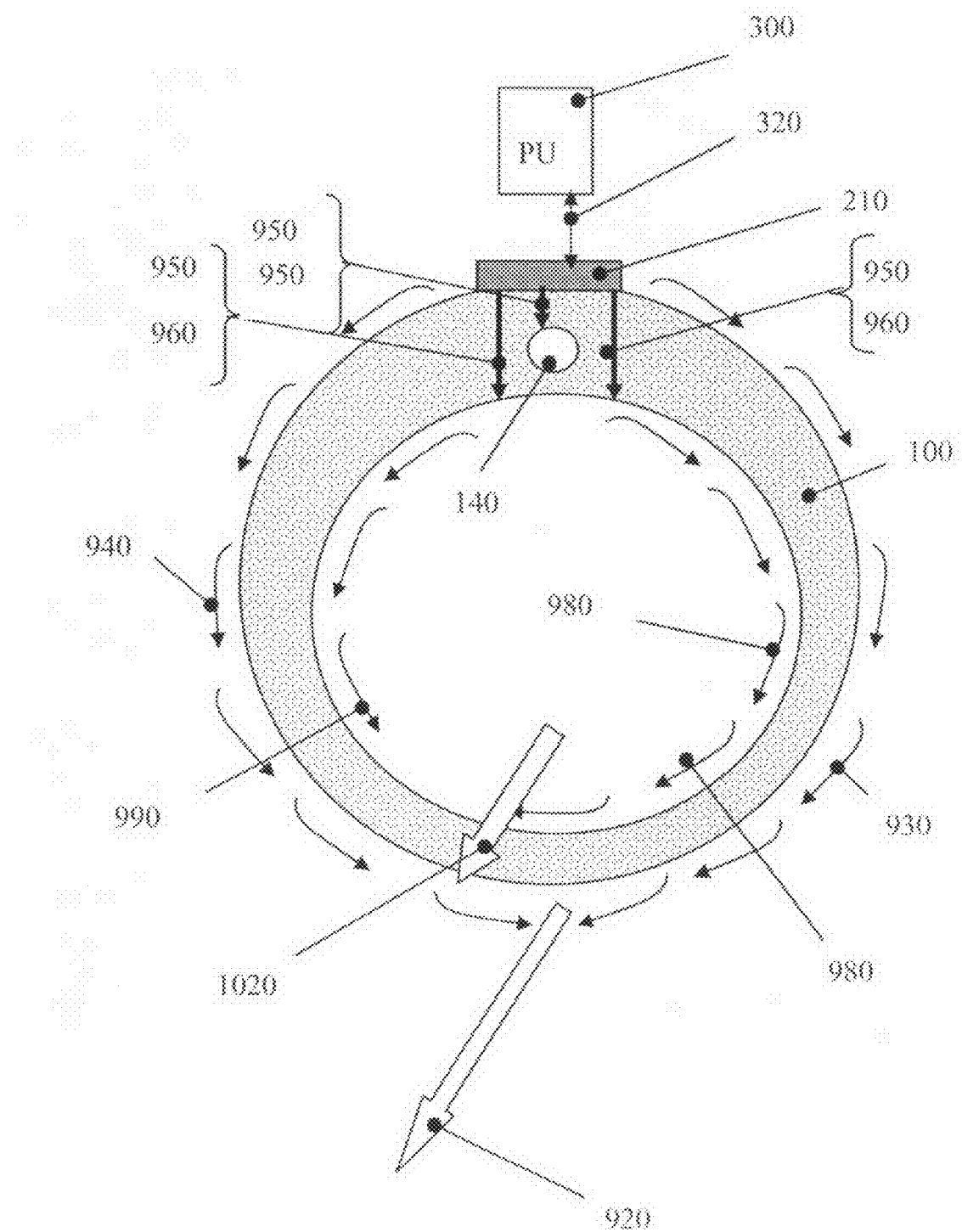
FIG. 7 is a cross section of SAW surrounding all of the surfaces of a urinary catheter.

Reference is now made to FIG. 7, which is a cross section of surface acoustic wave propagation along and around all the surfaces of the urinary catheter. At the first moment, the SAW runs surround the external catheter surface in 930 and 940 directions. After that, the wave propagates along the catheter surface in 910 (see FIG. 3) and 920 directions. Furthermore, part of the vibration energy is transmitted through the catheter material in 950 and 960 directions and reaches the inflation and internal functional channels. Here the energy propagates in directions 990 and 980, surround the internal channel, and in directions 1010 (not shown) and 1020, along the internal channel.

Resulting from the action of PZT element 210, surface acoustic waves propagate in at least one of two opposite directions from the actuator: towards the body, and towards the urinary bag. If it is required, the propagation of surface acoustic waves may be restricted to one direction only, by means of acoustic absorbers in the form of rings, which may eliminate propagation of acoustic energy. Such absorbers may be incorporated into the external or internal channel, or into the both.

Figure 8:
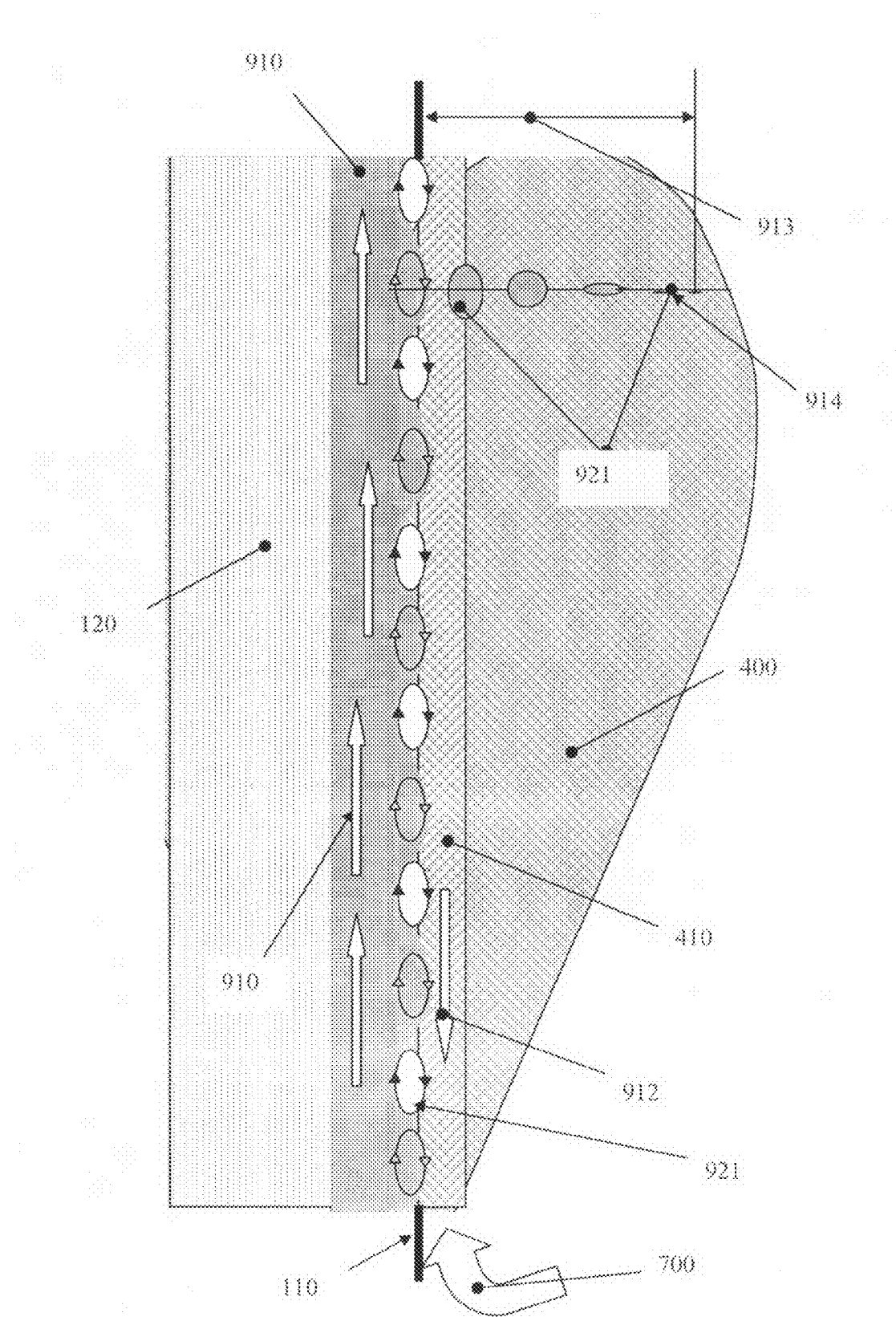
FIG. 8 illustrates a physical motion of SAW on a urinary catheter mechanically associated with time-dependent elliptical displacement of a surface and propagating transverse waves to body tissues when the device of the present invention is connected to a catheter.

Reference is now made to FIG. 8, which illustrates physical motion of surface acoustic waves in the direction 910 on the urinary catheter 100, which is associated mechanically with time-dependent elliptical displacement of the surface structure 911.

Between the catheter surface and body tissues 400, elastic organic materials (such as mucosa 410) appear. Bacteria enter into the body through these materials, as it is shown in FIG. 1, in direction 810. SAW propagates on catheter external surface 110 and mucosa 410.

Theoretically, SAW is combination of longitudinal and shift waves. Their vibration amplitude decreases exponentially with distance from this border. The energy of a surface acoustic wave (Rayleigh wave) is localized in a surface layer 913 from about $\lambda_R$ up to about $2\lambda_R$, where $\lambda_R$ is the length of Rayleigh wave. The physical motion of this wave type is associated mechanically with time-dependent elliptical displacement of the surface structure.

In one embodiment of the present invention, the depth of the propagated surface acoustic waves in the direction of the body mucosa reaches 2 wave lengths (less then 1 mm).

Surface acoustic waves cause micro motion of the particles (such as bacteria) and liquids on the catheter surface in direction 912 that is parallel and opposite to wave propagation direction 910. This phenomenon, created by surface acoustic waves, is characteristic to all materials and is effective in the depth of 913. The greatest micro motion in the direction 912 is at the near proximity to the surface, and it gradually disappears in the depths of 913.

As a result, bacteria on the catheter surface are forced to the exit orifice 700 of the body 400. The pushing direction 912 of bacteria contamination is opposite to their entrance direction 810 (see FIG. 2). The velocity of bacteria pushing out, in the case of this device, is about 1 mm/h, and this velocity is greater than the velocity of mobile bacteria On the other hand, the micro motion of the particles increases the pressure in the near tissues, eliminating bacteria entrance.

The shear vertical component 914, known as transverse energy of the SAW, causes periodic compression and rarefaction of the materials and fluids, resulting in transmitting of acoustic energy from the catheter into surrounding tissues. The relation for this is given by Victorov I. A., Surface sound waves in solids: Nauka Publishing, Moscow, 1981, p. 5-10, as a function of the surface wave length and share wave length.

The shear vertical component of the SAW results in micro massage. The effect may be understood as a mechanical effect of acoustic energy traveling through the medium and causing the molecules to vibrate. The above effects will probably influence the general state of the patient tissues and enhance healing processes in post surgery patients, by possibly enhancing tissue fluid interchange.

The transverse energy may be transferred to the tissues of the human body from external surface and to urine from the internal surface, preventing bacteria gaining intraluminally.

The transverse vibration energy affects the fluids in contact and the friction of the fluids is reduced; the vibration may expel the fluid and drying process at the point of contact with the body occur, which slows or prevents the entry of bacteria extraluminally.

In summary: the actuator creates an acoustic energy transmission line towards the liquid and body tissues in acoustic contact with urinary catheter, which may have two components: a) in depth equal to two surface wave lengths towards the body tissues, the tissue particles are mechanically-elliptically oscillating, with velocity of tenths meter/second; b) in depth exceeding two surface wave lengths towards the body tissues, the particles are lineally-mechanically oscillating, with nanometer amplitudes; Positive effects on tissues, followed by increased repair and healing processes, increased growth of capillary, increased ph of tissue liquids, lowered pain syndrome, micro massaging and etc. may be observed.

The actuator may apply short-term stress, so as to dislodge the bacteria from the catheter surface.

When the device is attached to the catheter and coated with antimicrobial material, SAW process propagating in the interface between the external catheter surface coated with antimicrobial layer and body tissue.

The known, based on chemical interference, technological solutions for biofilm prevention on medical device surfaces suggest action by hybrid polymer layers, such as surface treatment by antibiotics or silver ions: silver in alginate polymer; silver ion (PVD+IBAD); silver (PVD); silver ion implantation; silver/hydrogel; antibiotics in hydrophilic polymers; chlorhexidine and silver sulfadiazine. The principle of the action of the polymer coating has the following steps: 1. water diffuses into polymer coating; 2. Drug dissolves in water and diffuses out; 3. drug near the surface is removed quickly.

Due to different acoustic velocities in the materials (in our case, in the polymer layer and in tissue) the drug activation process may be managed while applying the device. Through managing the SAW process and varying the intensity of SAW energy, it becomes possible to control the intensity of drug diffusion.

When SAW is transmitted through interface micro motion process effects in cleaning out the polymer surface, in other words, the active polymer surfaces will not be covered with biofilm, and the efficacy of drug diffusion will be increased. The depth of SAW processes in the interface between polymer material/tissue, as well as the depth—in the interface between silicone material of catheter/polymer material, are related on actuator frequency.

By means of variations in SAW process intensity (increasing/decreasing SAW amplitudes), drug dissolvent and diffusion may be controlled The effect may be applied for different coats based on active element (silver ions, antibiotics, etc) diffusion from the coat layer.

Furthermore, when the internal and/or external surfaces of the urinary catheter are coated by copper or silver alloy, silver hydrogel, antibiotic coat, or any other sort of antimicrobial coat, the device thereby prevents bacteria adhesion and biofilm formation on these antimicrobial surfaces, increasing antimicrobial action time of the coating agents. In this case, when surface acoustic waves are applied in the interface between the catheter material (for example: latex) surface and the coating layer, thereby influencing the antimicrobial agent activity, control of the velocity and time of this agent illusion may be achieved.

On the other hand, when acoustic waves are applied in the interface between the coating layer and body tissues, the result may be prevention of contaminations on the surface and, by this increasing antimicrobial action time and activity of the coating agents, controlling the velocity and time of this agent illusion. In the case when surface acoustic waves are applied to both interfaces, namely between the catheter material (for example: latex) surface and the coating layer and between the coating layer and the body tissues, the above actions are increased. Either or both of the internal and external surfaces of the urinary catheter may be coated by copper or silver alloy, silver hydrogel, antibiotic coat, or any other sort of antimicrobial coat, and the balloon (stabilizing or therapeutic) resonance (due to compression waves) thereby increases antimicrobial action on tissue healing processes This is in addition to the actions of the device in preventing bacteria adhesion and biofilm formation on these antimicrobial surfaces and increasing antimicrobial action time of the coating agents.

Figure 9:
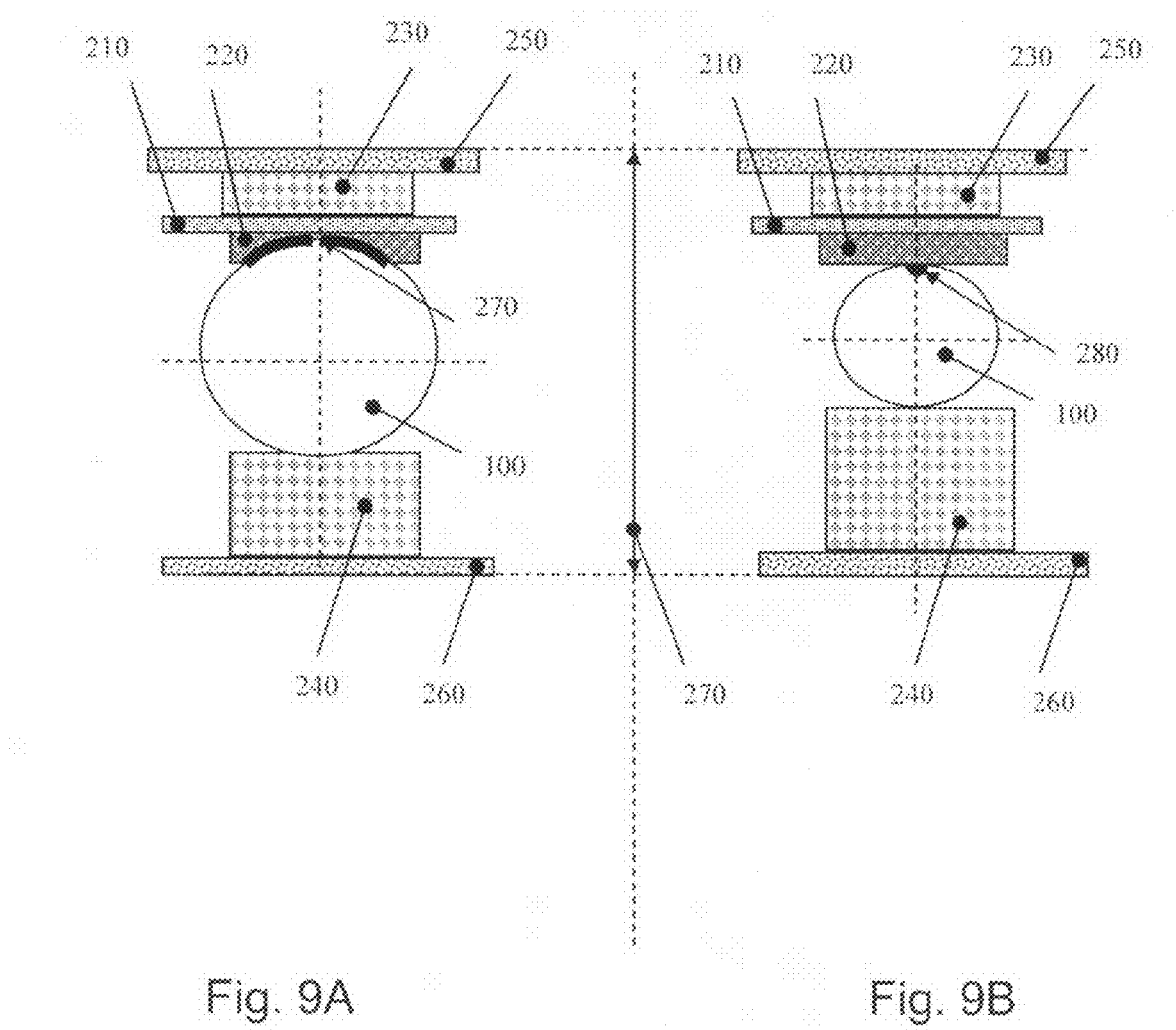
FIGS. 9A and 9B are schematic illustrations of coupling the device of the present invention to a catheter having different diameters.

Reference is now made to FIGS. 9A and 9B, which are schematic illustrations of the coupling of the device's actuator 200 to urinary catheters 100 of different diameter. The action of the add-on device of the present invention is based on acoustic pressure generation by an actuator on the surface of a urinary catheter. In medical practice, different diameters of catheters are used. For catheters having a smaller diameter, the smaller acoustic energy is needed to be generated in comparison to catheters of larger diameter, resulting in the same acoustic pressure amplitude. The said may be achieved in two ways:

1. through adjustment of acoustic energy transmitted from PZT element controlling by driver output. This method is confusing because of possible medical personal subjective mistakes.
2. through self-adjustment of the device by choosing construction method shown in FIG. 9. The self-adjustment concept is based on application of an elastic acoustic layer 220 between PZT actuator 210 and catheter 100. The catheter is preloaded with springs 230 and 240, which are attached to the lower 260 and upper 250 surfaces of the case, respectively, so that catheters of all diameters may be used. Relative acoustic energy transfer area from PZT element 210 to external surface of the catheter depends on the contact area.

When different diameter catheters are introduced, the spring elements 230 and 240 are compressed with different force. As shown in FIG. 9A (for a catheter with a larger diameter), the elements 230 and 240 are compressed to a greater extent than they are compressed in the case shown in FIG. 9B (for a catheter with a smaller diameter). In such a manner, the contact areas 270 (for a catheter with a larger diameter) and 280 (for a catheter with a smaller diameter) between layer 220 and catheter surface 100 are varied, and the larger diameter catheter has a larger contact area than does the smaller diameter catheter. The result is that the larger diameter catheter gets more acoustic energy than does the smaller diameter catheter. The larger diameter catheter has the larger contact area than does the smaller diameter catheter, and the resultant acoustic energy on both catheters is approximately equal. The acoustic energy shift for catheters with different diameters (ranging from No. 8 to 22) is about 10%

Figure 10:
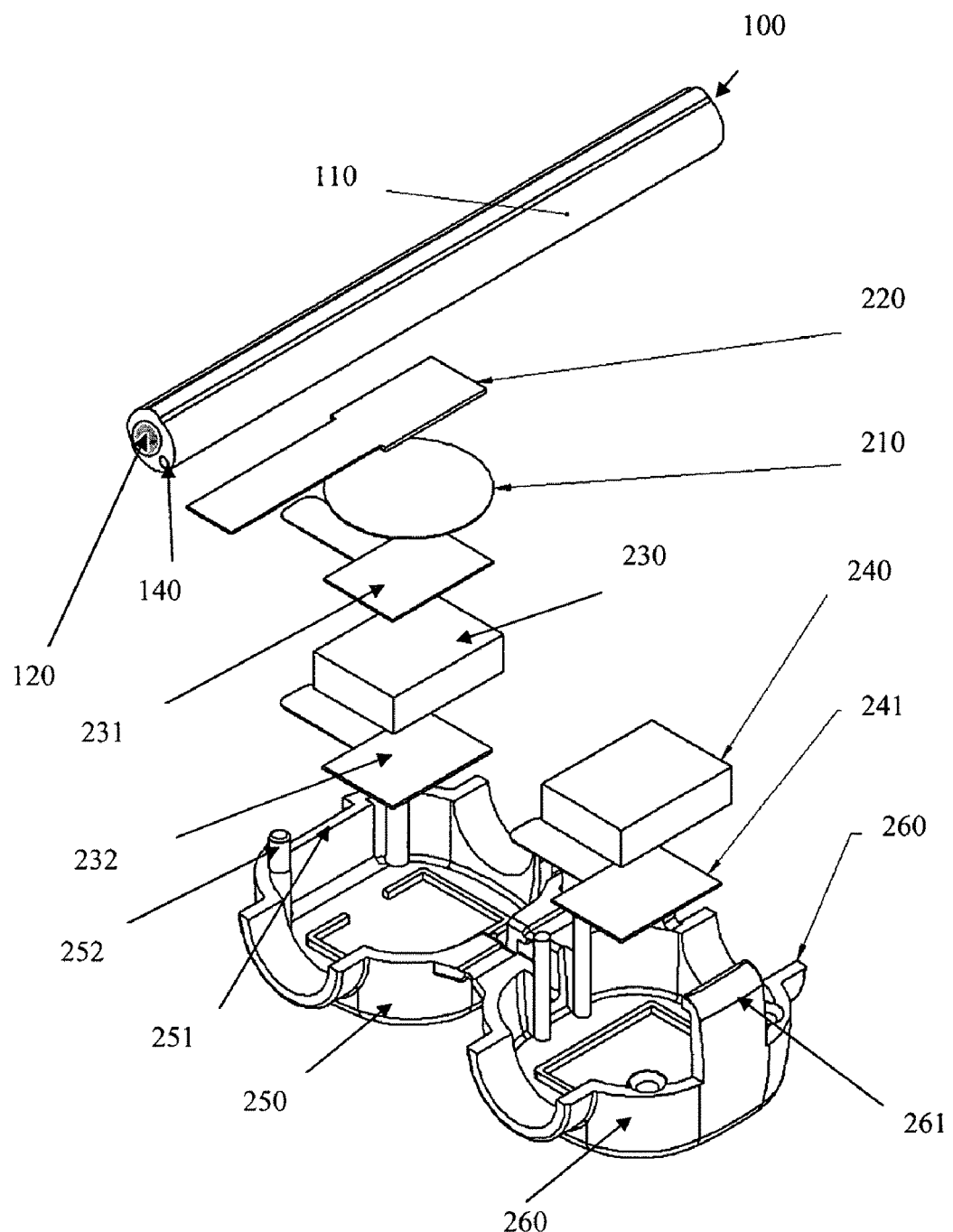
FIG. 10 is a schematic illustration of the actuator construction and components.

Reference is now made to FIG. 10, which is a schematic illustration of the device actuator construction and components. The system of the inventive device, as illustrated in FIG. 1, comprises two components which include a disposable actuator 200 and driver 300. The actuator 200 is a disposable, small, light-weight clip-on actuator that is attached to the Foley catheter. The disposable actuator 200, as shown in FIG. 10, comprises a housing or case that is made from two opening parts 250 and 260, which are packed and prepared for use in opened state.

The production procedure contains steps: sticking the stickers 241 and 232 inside the actuator case on two parts 260 and 250, and sticking the foam members 240 and 230 on the glued surface of stickers 232 and 241. On the foams should be attached new stickers 231 and 220, but the upper protective paper from the sticker is not yet removed. The PZT element 210 is arranged into the plastic case part 250 in the designed space. The protective paper is removed from the sticker 231 and the ceramic element 210 is attached to it. The sticker 220 is then stuck onto the PZT element, not removing the protective paper from sticker 220.

In one embodiment, the actuator dimensions are: 42 mm×29 mm×15 mm and the actuator weighs 5 grams alone and 20 grams with the cable.

When in use, the protective paper is removed from sticker 220, the catheter 100 is fixed on the glue layer of sticker 220 so that its ends are fixed in special grooves, and by means of alignment and locking mechanism 252 the case is closed.

Figure 11A:
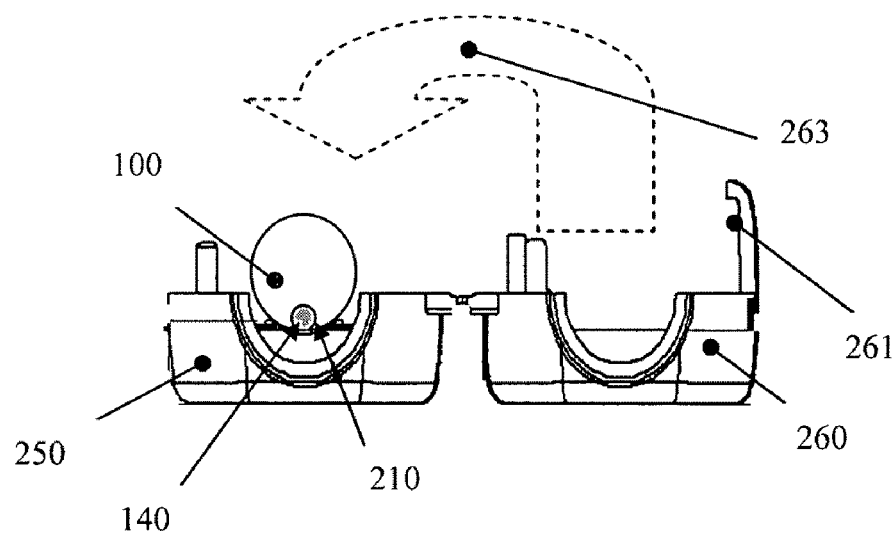
FIGS. 11A and 11B are illustrations of the way by which catheter is secured on the actuator
Figure 11B:
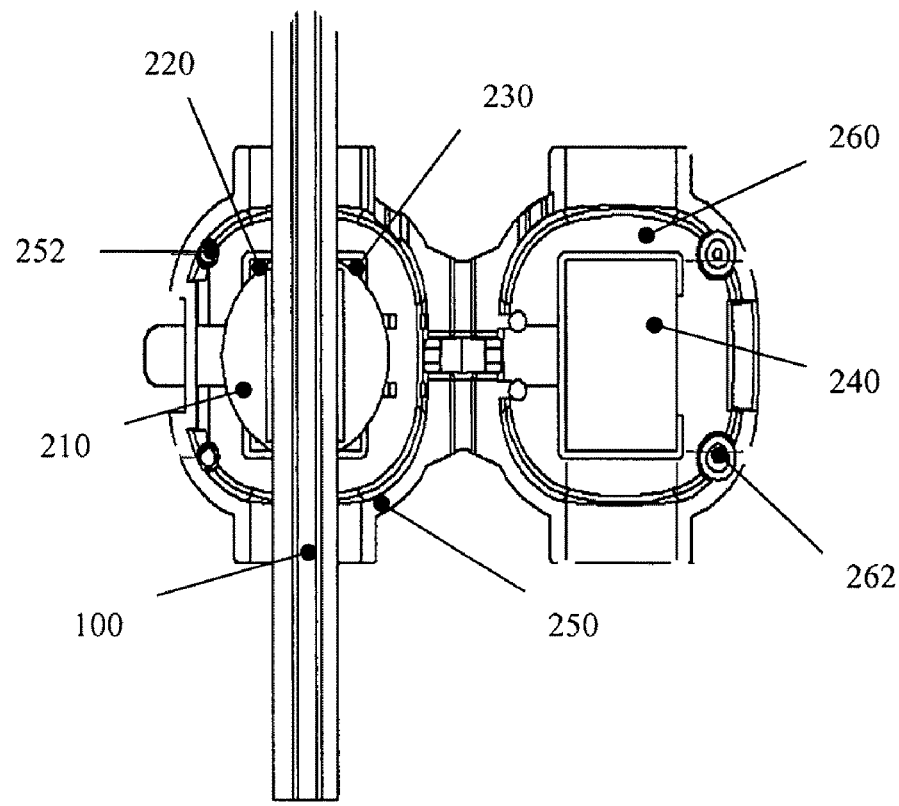

Reference is now made to FIGS. 11A, 11B, showing catheter 100 fixation in the actuator case. When catheter 100 is placed in the case part 250 on glue layer of sticker 220 within inflation channel 140 on the PZT element 210, the second case part 260 is closed in the direction of arrow 263 and anchoring mechanism 261 closes the case with strips 262 entering to holes 252. Catheter is fixed and acoustic preloud enabled due to glue layer 220 and foam 240.

Reference is now made to FIG. 12A-D, which shows thin disk shaped PZT element 210. In one embodiment, element 210 has dimensions: length 211, width 212 and radius 213, dimensions: 26×26×0.10 (mm). In one embodiment, the actuator should be fixed to the catheter in the direction along the length 211.

The gluing tape (sticker) 231 is on one side fixed to one side of the PZT element and on the other side is glued to the springing material 230. The gluing tape 231 can have a consistent shape or may have several portions, resulting in increased bending vibration amplitudes of PZT element acoustic intensity. The effect may also be achieved by means of manufacturing the PZT element with portions of piezo ceramic material on a metallic base, or (in another case) metallic base may have holes.

In one embodiment, the said PZT element 210 is coated with a silver electrode on one side and with thin metallic layer on the other side, and in one embodiment the diameter of said metallic layer should be equal to or exceed the piezo element diameter.

In one embodiment, the range of the piezo ceramic oscillations frequencies is about 1 Hz-about 10 MHz. The waves are generated in a longitudinal and bending vibration modes by a piezo resonator having a polarization axis perpendicular to the surface of the catheter. The waves are generated by a piezo ceramic material joined to a metal material into a bimorph element, each material being present in a layer at a respective thickness ratio about 0.95-1.35.

The electrodes are divided with non-conductive places, which may be parallel or non-parallel to the polarization direction, and the single phase, two-phase, or multi phase electrical signal may be sent from the driver to the electrodes. In addition, by means of different connections between electrodes, longitudinal, bending and thickness vibrations may be excited simultaneously or separately.

Another side of PZT element, as it is shown in FIG. 12B, is glued with double side paper sticker 221 having a small tongue 220. When removing protective paper from the sticker 221 at the moment of affixation to the catheter, sticker 221 remains with glue track 222 (see FIG. 12C) having a section of rippled material 223 in its center part. The rippled material 223 at the coupling moment enters into the elastic silicon material of the catheter and secures the actuator to the catheter surface.

Piezo resonator transforms electrical signals to mechanical vibrations which excite surface acoustic waves featuring mechanical vibration amplitudes in the 0.1-0.3 nm range, the said surface waves propagating along the catheter surface. The vibrations of the actuator piezo element may be applied in multi-modes: thickness, longitudinal, and their combination.

Figures 12, 12A:
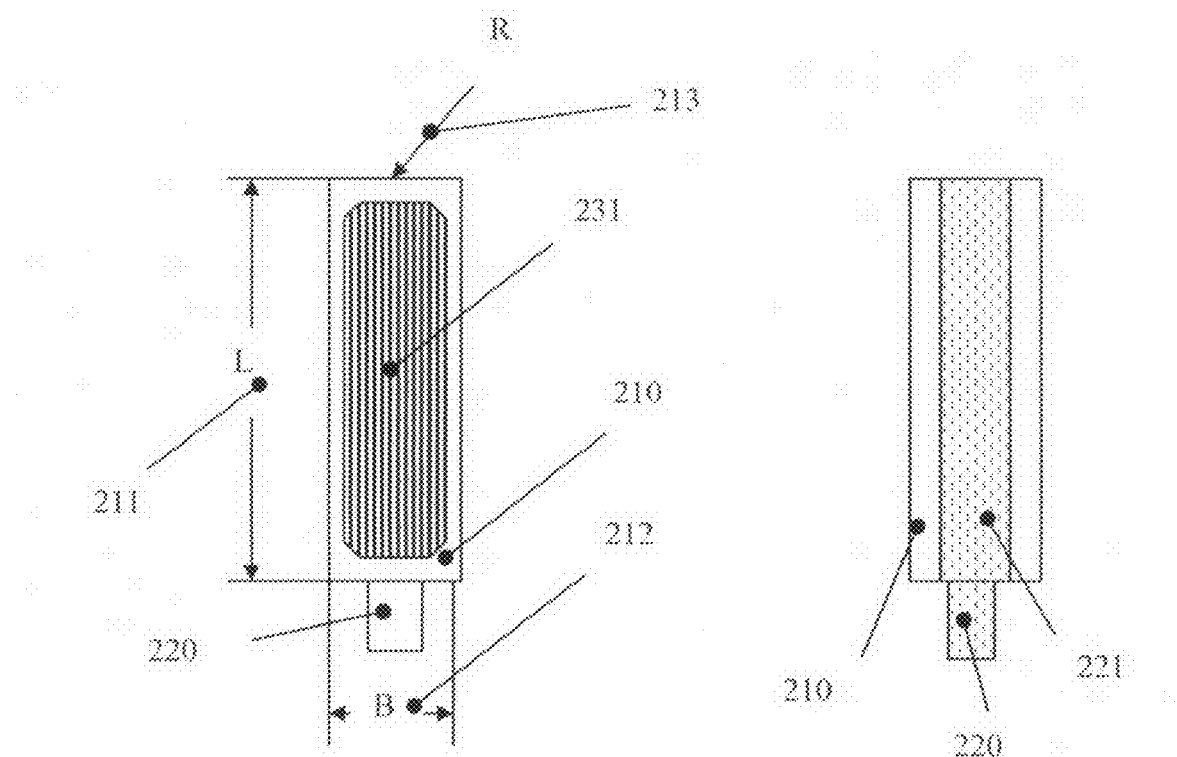
FIG. 12A shows a thin PZT element.
Figures 12C, 12D:
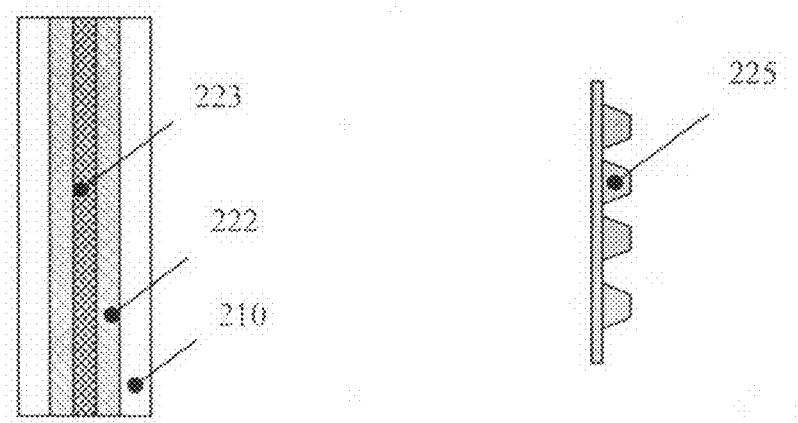
FIG. 12C shows the sticker with a glue track, which has a section of rippled material in its enter.
FIG. 12D shows stabilizing needles in place of the rippled material.

FIG. 12D shows, as described above, the case when stabilizing needles 225 are used to play the same role of the rippled material and such coupling eliminates actuator slipping, when the catheter is wet (such as during or after surgery, hygienic procedures, etc.). These micro needles are of about 5-about 100 micron dimension, may have a cone or fiber shape and may increase acoustic contact when SAW is created on the external and internal surfaces.

Once the urinary catheter has been placed into the patient's bladder in a standard fashion. the actuator wrapping is opened. The actuator can be used with all urinary catheter sizes. First, one gently pulls on the urinary catheter. Then, 2 to 3 cm should be estimated or marked away from the point at which the catheter exits the body. With the actuator body open, the tape strips should be peeled off both sides of the actuator. While insuring that there are about 2 to 3 cm of catheter between the actuator and body of patient, the actuator should be placed over the catheter, so that the catheter enters and exits the actuator in the semi-circular grooves at each end. Once the catheter is in place, the actuator body should be closed such that the two sides snap together. The connector is inserted at the other end of the actuator active cord into the driver output socket.

Figure 13:
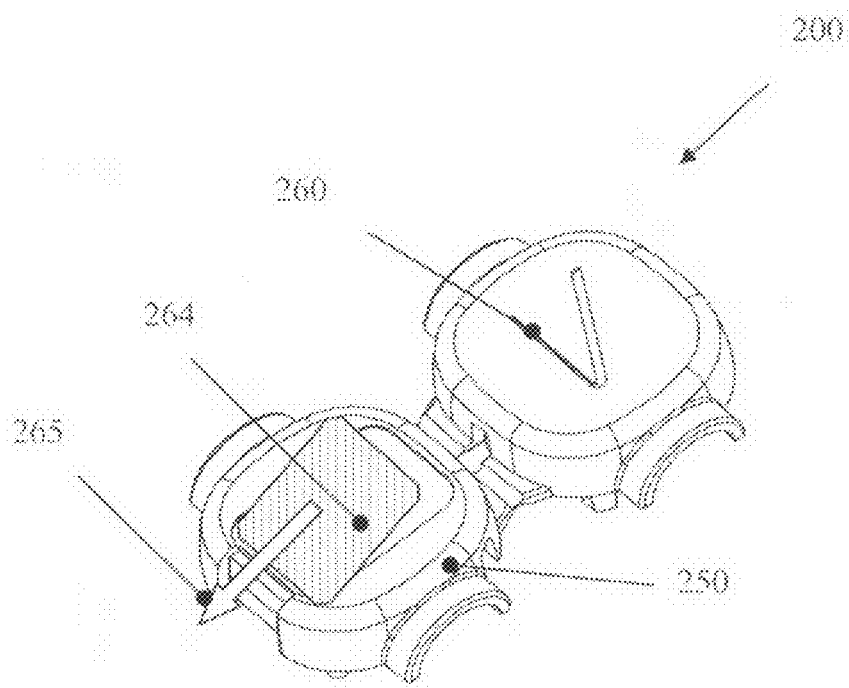
FIG. 13 illustrates a releasable anchoring system containing the actuator attaching a catheter to a patient's leg

Reference is now made to FIG. 13, which schematically shows the device configured for the option of attaching the actuator to a patient's body. The attachment system 264 comprises a two sided adhesive tape, which is by one side attached to the actuator case part 250, which is in touch with the patient's body (e.g., leg). The attachment system may be of the same size as an actuator case, or may be bigger, if the use is prolonged. The protecting paper layer 265 should be pulled of and the actuator anchored to the patient's leg by means of the medical grade glue layer which is situated under the protective paper 265 of the attachment system. Such a securement system obviates the need for attaching the catheter by tape, which is currently being used in practice. The securement system may be specially designed to achieve custom aid attachment of the actuator to the patient's leg based on medical disposable pad principles.

Figure 14:
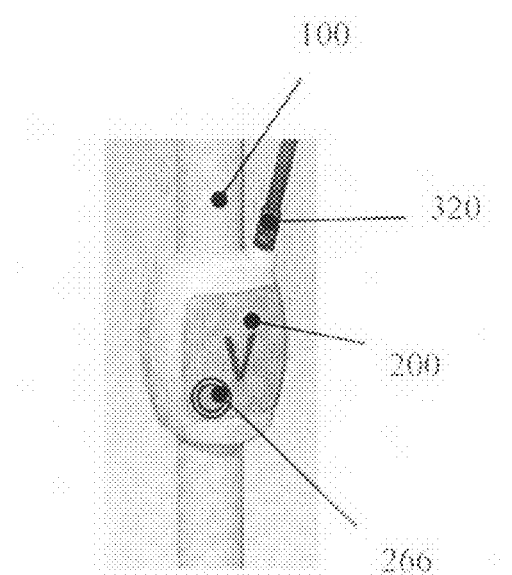
FIG. 14 is the actuator of the present invention showing a hole for checking the acoustic output of the actuator.

Reference is now made to FIG. 14, which illustrates a special hole or aperture 266 formed in the actuator case 200, said hole being made for acoustic output measurements of the actuator by means of contact or non contact methods. Contact measurement will be used when the device will work in high frequency regime of 1-50 MHz. The non contact method will be applied when the work regime is less then 1 MHz and is based on acoustic propagation through pressed air.

As some physicians wish to stabilize the Foley catheter to the patient's leg, a simple method of stabilization using standard medical grade FDA recognized tape may be used. For example, a double woven breathable medical grade tape/patch cut into a butterfly shape may be used. A small amount of circular a double-sided adhering material, such as hook-and-loop elements, commonly known as Velcro®, can be placed on the patch and on the actuator to stabilize the actuator to the patch in a stable but reversible fashion. The skin can be cleaned off, e.g., with Betadine, and then the patch is placed on the leg. The actuator can then be placed on the Velcro® portion of the patch. When the patch is removed, it is preferable that alcohol is used.

Figure 15:
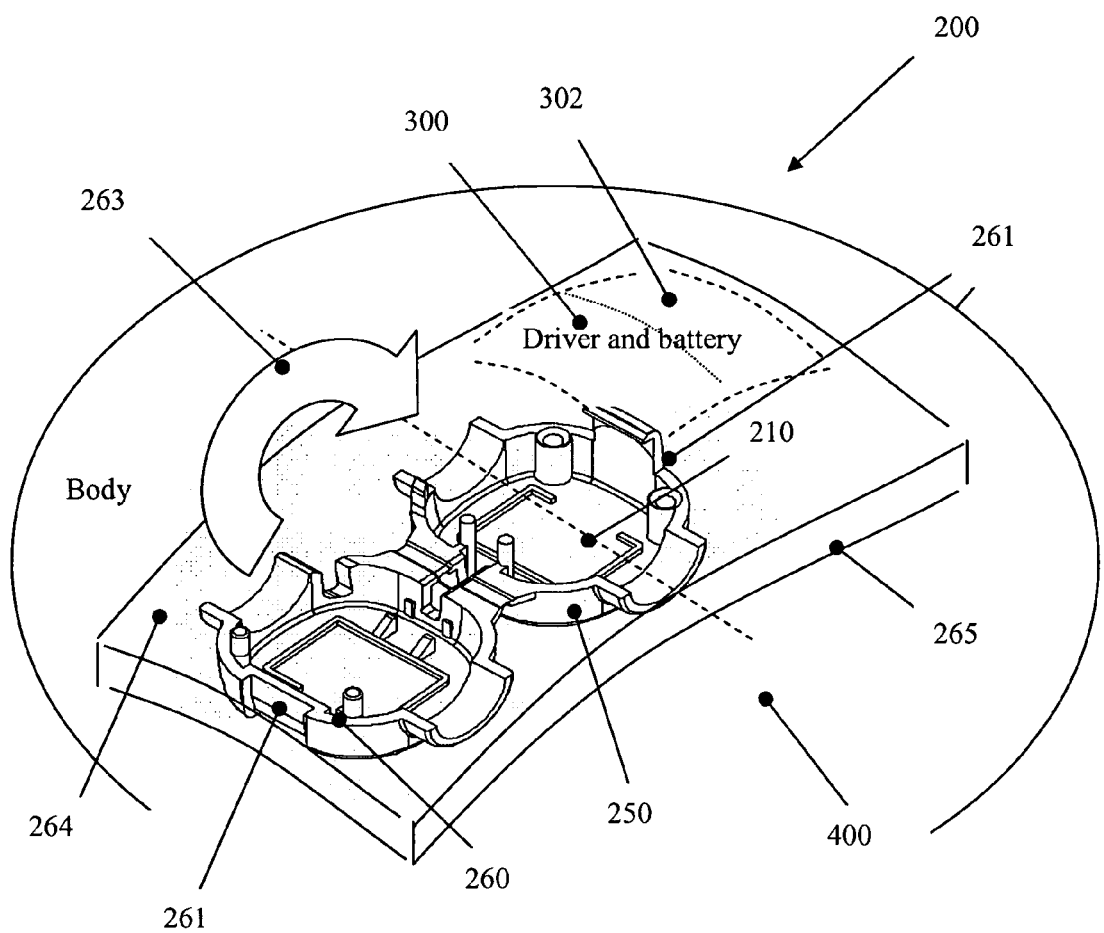
FIG. 15 shows the actuator in patch configuration

Reference is now made to FIG. 15, which illustrates another version of the device in a flexible patch configuration, for example an actuator encompassed into detachable patch and connected with the driver, wherein vibration energy is transferred to the catheter surfaces and has therapeutic impact due to acoustic energy. The device may have several different configurations One of them may have an option to be detachably adhered to the patient's leg (e.g., by means of medical grade adhesive tape), or to be attached in any other manner (for example, via adjustable belt which is closed with an adhering mechanism, such as a clasp or hook-and-loop elements).

The principle description of the flexible patch configuration is shown in FIG. 15. The flexible battery 302 is incorporated with flexible electronic unit 300 and they are configured in separate layers of the detachable patch 264, having adhesive bottom 265. The actuator's PZT element 210 is placed in a plastic case 200, having two sides 260 and 250. When the patch 265 is adhered to the patient's leg 400, the catheter 100 is placed into the special fitting, and lock mechanism 261 locks the catheter to the patch.

The length of the catheter part between patient's body and latch is long enough and does not mechanically push the catheter out of the body.

The plastic case 200 is detachably placed on the patch 264 top using an adhering mechanism, such as a clasp or hook-and-loop elements or using any other known clip-on mechanisms, which allow movement of the case relative to the patch.

The driver unit in a patch configuration may be a chip device or flexible CPU system, configured on the patch basis, and electrically connected with a flexible battery which is based on the same patch. This disposable device may have a rechargeable flexible battery, or all the parts including the battery may be disposable.

The patch configuration eliminates the need of the driver and the actuator to be separate parts of the device. Driver and actuator may be integrated into one flexible part based on the securing patch.

The patch may also enclose wireless regulation feature, enabling medical personal to switch on and off the device when it is needed, and to regulate the acoustic intensity depending on patient status, on drugs, and other considerations.

In addition to the main function, actuator may transmit acoustic energy through the patch material to the human skin under the patch. These vibrations cause micro massage at the location of adhesion, thus reducing, and perhaps eliminating, irritation of the skin and making it easier to pull the patch material off after use.

The following are alternative variations of the main patch:

The patch comprising a medical grade patch, the actuator and one of driver options (stand alone box and chip on the patch), battery options (changeable, rechargeable, disposable—for short period, for ex. two days).

The patch for stabilizing a urinary catheter, containing medical grade adhesive patch material, which is by attached on one side to the patient leg and on other side to the actuator using an adhering mechanism, such as Velcro® material. The actuator is electrically connected with driver box.

The same patch with the actuator case incorporated into the patch by special manufacturing procedure.

The patch ensures two functions: stabilizing the urinary catheter and preventing trauma which may occur if the catheter is pushed, and exciting SAW on the catheter surfaces, preventing biofilm formation, minimizing trauma of indwelling devices to the body tissues.

The patch may be manufactured as a water resistant device. The main requirement for this construction is to enable acoustic contact between the PZT element and the catheter surface. Such a water resistant device may contain two parts. The first part is attachable to the body, and the catheter is secured to this part. The second part containing the actuator, driver and battery is put on the first part as a sandwich type construction. The opposite case, when the active elements are incorporated into the first part, is also possible. Other constructions are also possible, enabling the production of a disposable device. The materials for active urinary patch are those used in the patch production (e.g., 3M, Tyco, Venetec, Kimberly Clark, J&J)

The merit of the patch configuration is that the device is user friendly, needs no long wires connecting actuator and driver, does not disturb the movement of the patient and secures the device to the patient body, preventing the possibility of the actuator slipping on the catheter surface. In addition, the patch configuration solves the problem of possible abrasion to the patient's skin, which may be caused when the catheter with the add-on device is mechanically pulled due to patient or care personal activity.

Figure 16:
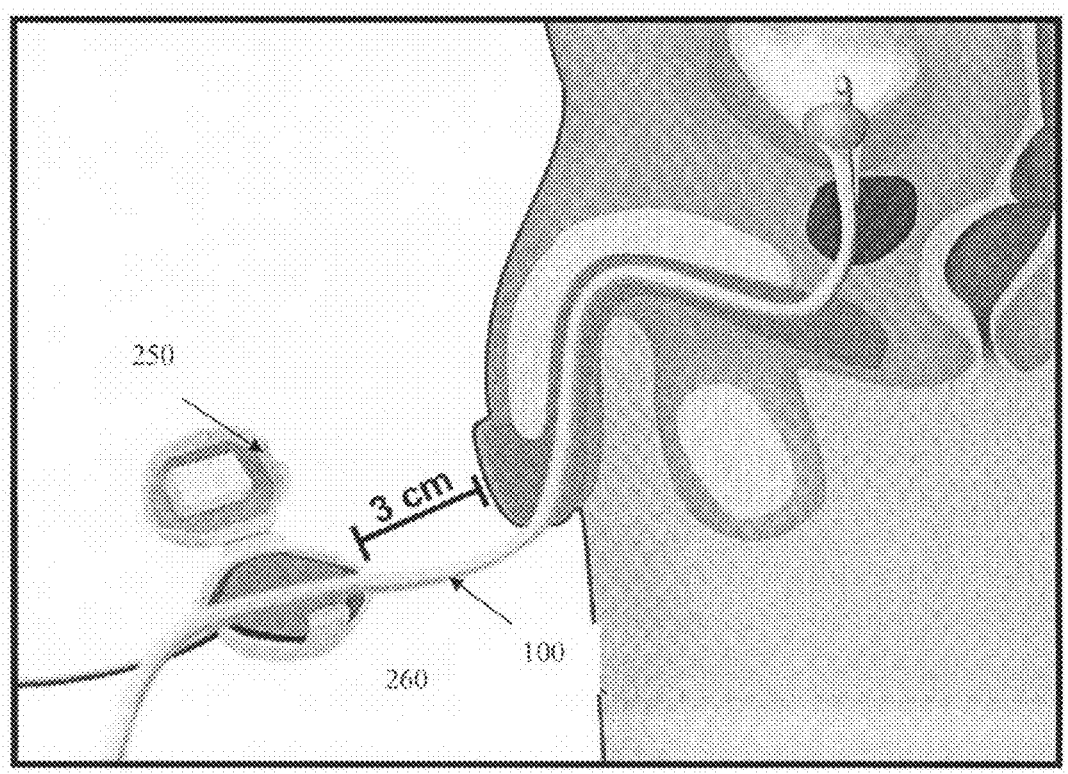
FIG. 16 is a schematic illustration of applying the present invention.

Reference is now made to FIG. 16, which schematically shows the placement of the device 250 at a distance of 3 cm from the patient body, when the catheter 100 is introduced to the patient's urinary tract. The catheter 100 is placed on the piezo element and the actuator case is closed, e.g., by a clip on device.

Experiment 1

We examined the correlation between levels of SAW energy that were applied and the *E. coli*-induced RBC aggregation. SAW activated with 0.05-0.2 mW/cm² effectively prevented RBC aggregation (the methods and results are described below) and were used for the energy requirements.

Figure 17:
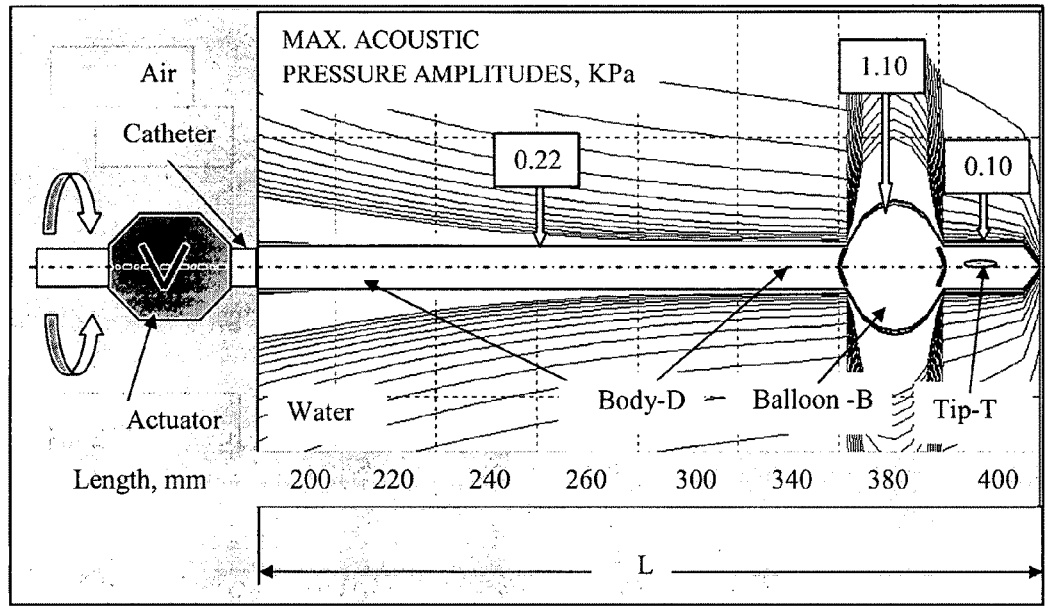
FIG. 17 is a simulation of the acoustic pressure amplitude distribution on the surface of a urinary catheter having the present invention attached.

Reference is now made to FIG. 17, which is a simulation of acoustic pressure amplitude distribution on the surface of a urinary catheter 100 with actuator 200 attached. The maximal acoustic intensity on the urinary catheter was determined using a high performance hydrophone measurement system (HP series, Precision Acoustic Ltd). This system, designed for in water measurements of high frequency acoustic pressure amplitudes from emitting points, was applied to the urinary catheter section using 1 mm diameter hydrophone needles. The maximal acoustic pressure amplitude $P_{max}$, measured when electrical signals in a frequency of 100 KHz were applied, was $P_{max}=1.1$ KPa (kilo Pascal), and the value of the spatial peak temporal average ($I_{SPTA}$) in water was: $I_{SPTA}=0.165$ mW/cm². The same values correlate to acoustic energy levels on the catheter balloon 150 (shown in FIG. 6).

This value is three orders of magnitude smaller than the maximal acoustic output limit for diagnostic Doppler instruments (CW) $I_{SPTA}=500$ mW/cm² (14).

The acoustic pressure amplitudes of the coating nanowaves at different parts of a urinary catheter (body, balloon and tip) were determined using a high performance hydrophone measurement system. The largest transversal vector directed perpendicular to the catheter surface, is detected around the balloon. The max. acoustic energy levels (max. acoustic pressure amplitudes, KPa) for different catheter parts were measured with hydrophone measurement system and performances were the following: D—Body—0.22 KPa; B—Balloon—1.10 KPa; T—Tip—0.10 KPa.

The energy, as it was measured on catheter body part (0.22 KPa), is actual to all catheter lengths 170 following the urinary bag direction.

Figure 18:
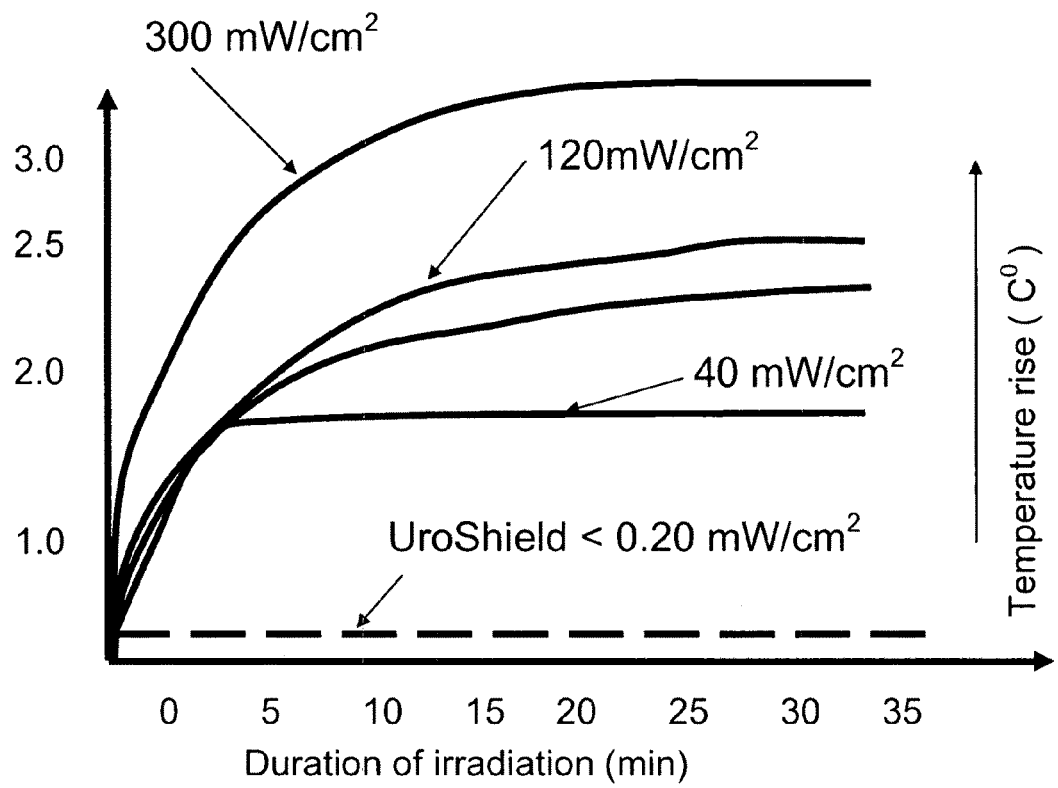
FIG. 18 is a schematic illustration of the temperature rise in a mouse fetus during the sonation of the mother as compared with to the acoustic level transmitted by the present invention.

One biologically relevant ultrasound exposure quantity is related to the possibility of tissue heating as ultrasound is absorbed by tissue. This is so called terminal mechanical index. Reference is now made to FIG. 18, which is a schematic illustration of temperature rise in mouse fetus during sonation of the mother compared to the acoustic level transmitted by the add-on device. Using the add-on device, virtually all the acoustic energy generated by the source (activated catheter) is transmitted into the patient's body and is here converted into heat. The diagram below compares temperature rise dependent on the duration of acoustic energy applied, as shown in FIG. 18.

It is seen that applying ultrasound energy level $I_{SPATA}$ of 40 mW/cm², the temperature increases with the time at first 5 min., and approaches the rise of 1° C. As time goes on, the acoustic energy has no further influence on the temperature rise. The same effect multiplies for other energies, as it is shown. Based on the graphical dependence shown, in our case, 200 times lower energy level $I_{SPATA}$<0.2 mW/cm², may have negligible effect on temperature rise, as shown in the graph. The conclusion is that the device of the present invention is unlikely to produce any negative bioeffects on tissues and has a negligible thermal effect in body tissues In summary: The mechanical vibration energy is generated by a piezo element, achieving the pushing or pulling of materials including fluids and particulates suspended therein along the surfaces of the catheter. The vibrational energy may be of a kind sufficient to stimulate or release nitric oxide from at least small areas of targeted organs or tissues. SAW induced on urinary catheter material may prevent bacteria virulence occurrence and result in antibiotic use reduction for treatment. Wherein the vibrational energy reduces existing biofilm and augments effectiveness of antibiotics against the biofilm and produces antimicrobial and antithrombogenic surfaces. SAW induced micro streaming and effect in wound healing process. The vibrational energy inhibits infections of inner organs in acoustic contact with catheter. Vibrational energy increases slipping of the catheter and lowers the coefficient of friction, thereby preventing injury, irritation, or inflammation to the patient and to facilitate medical and surgical procedures.

Experimental Results

The experiments were done in Nanovibronix Ltd. Nesher and Sheba Medical Center, Tel-Hashomer, Israel.

A surface acoustic nanowave-generating device capable of transmitting acoustic vibration energy to indwelling catheters was constructed. A battery powered electronic driver delivers periodical rectangular electrical pulses to an actuator harboring a thin piezoceramic plate. The electric pulses produce piezoelectric effects which generate high frequency micromechanical vibration energy in the actuator at frequencies of 100-500 kHz with acoustic intensity of 200 mW/cm² and amplitudes of 300-800 nanometers.

The acoustic pressure amplitudes of the coating waves at different parts of a urinary catheter (body, balloon and tip) were determined using a high performance hydrophone measurement system. A simulation of the measurements is shown in FIG. 17. The largest transversal vector directed perpendicular to the catheter surface, is detected around the balloon with a maximal power intensity not exceeding 0.2 mW/cm². The acoustic waves in this system are non-cavitational, as the power levels applied are three orders of magnitude lower than the thresholds which produce cavitation (vibration frequency f=100 kHz at acoustic intensities of $0.5-2 \times 10^3$ mW/cm²).

Surface Acoustic Waves Interfere with Adhesion of Planktonic Microorganisns to Surfaces Our analyses of mechanisms by which SAW interfere with bacterial biofilm formation focused on the hypothesis that adhesion of planktonic bacteria to surfaces, the first step in the biofilm formation process, is the SAW target. We used the mannose receptor-specific adhesion of uropathogenic *E. coli* bacteria to guinea pig erythrocytes via the FimH lectin on type 1 pili, which culminates in RBC aggregation, as a model for evaluating SAW effects on bacterial adhesion.

Figure 19A:
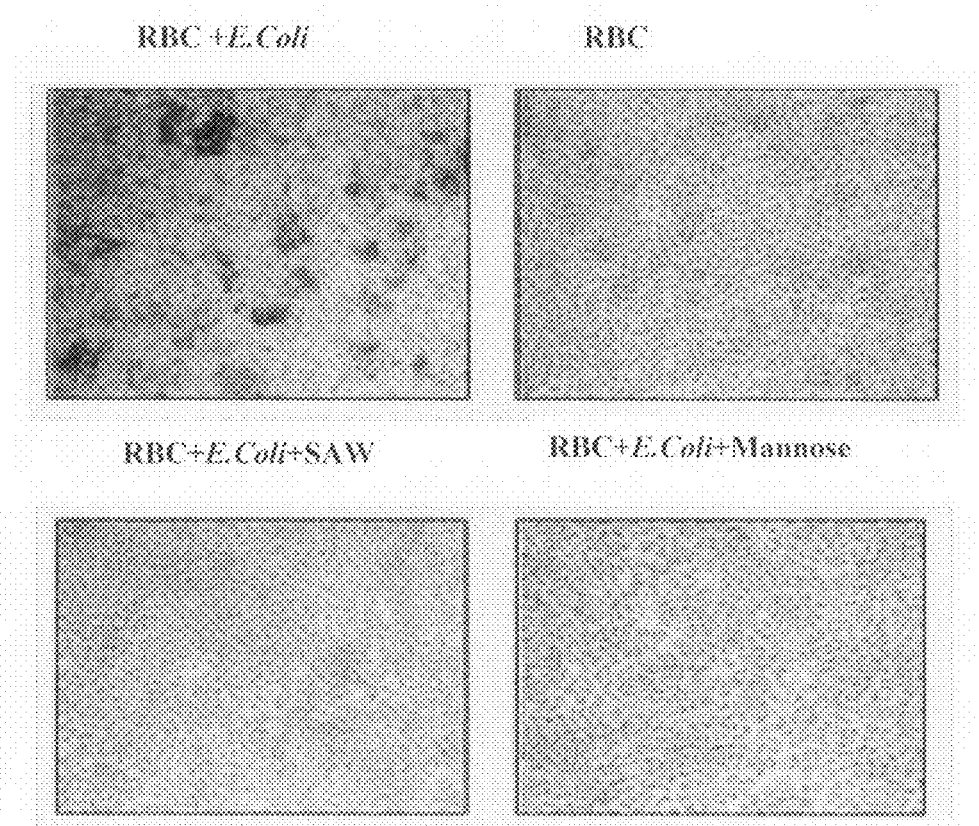
FIG. 19A shows the surface acoustic waves effective to completely prevent RBC aggregation.

Uropathogenic *E. coil* bacteria were co-cultured with guinea pig RBC in 50 mm Miniplast Petri dishes to which vibration energy-generating actuators were attached to the external bottom surfaces. Power intensities of 0.1 and 0.2 mW/cm2 which generated vibration frequencies of 95 kHz and 220 kHz with acoustic pressure amplitudes of 0.1 and 0.22 kPa, respectively (equivalent to those measured on the tip and body of the urinary catheter), were applied. Bacterial adhesion-mediated RBC aggregation was monitored at several time points. RBC aggregation became detectable in control dishes 12+3 min after administration of the bacteria and monitored through three hours. FIG. 19A shows that SAW completely prevented RBC aggregation at these two power intensity outputs throughout three hours of follow up. The findings support our hypothesis that SAW interferes with lectin mediated adhesion of planktonic bacteria to substrates.

We deactivated the SAW treatment and continued to monitor the plates with time lapse photography. Guinea pig erythrocyte aggregation resumed 10+4 min. after SAW termination, a rate similar to RBC aggregation in control plates (12+3 min, difference not significant). These findings indicate that inhibition of RBC aggregation by SAW is mechanical, readily reversible following SAW deactivation and does not diminish the functionality of the FimH lectin on fimbriae. The bacterial mechanism for adhesion to RBC and other cells is, thus not damaged by SAW. Once aggregation has taken place RBC aggregates could no longer be dissociated by resumption of the SAW treatment (not shown) although it was reversed by Dmannose.

Figure 19B:
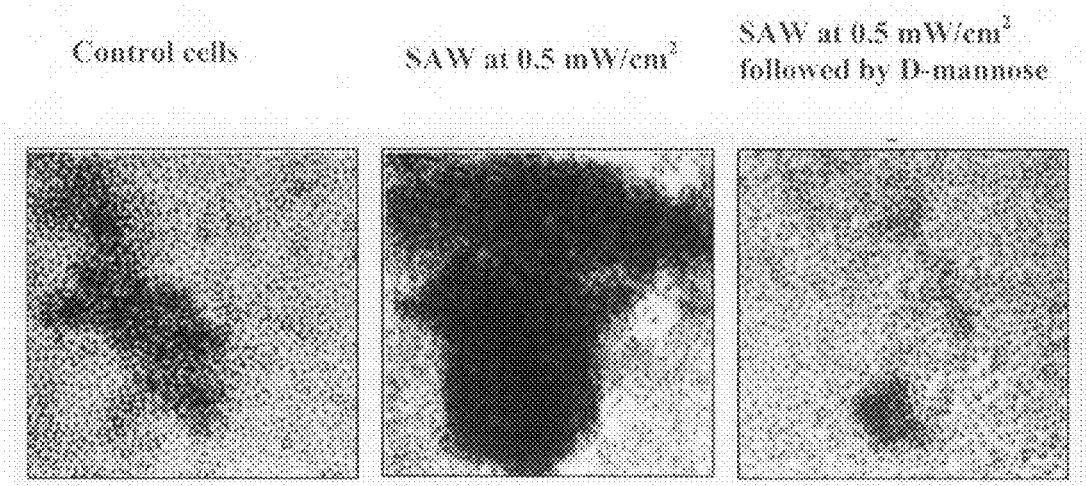
FIG. 19B shows the formation of exceedingly large RBC aggregates.

We next examined the correlation between levels of SAW energy that were applied and the *E. coli*-induced RBC aggregation. SAW activated with 0.05-0.2 mW/cm2 effectively prevented RBC aggregation, as shown in FIG. 19A. However, increasing the output to beyond a 0.35 mW/cm2 threshold converted the inhibition into a significant enhancement of bacterial attachment. Exceedingly large RBC aggregates formed as shown in FIG. 19B (middle panel), which were susceptible to dissociation with D-mannose (FIG. 19B right panel) and gradually dissolved upon cessation of the SAW treatment (not shown). Hence, high frequency SAW applied at power intensities beyond a threshold of approximately 0.35 mW/cm2 can activate FimH force sensor activity in a manner similar to force sensor activation seen when shear force is applied to uropathogenic *E. coli* bacteria.

Prevention of Microbial Biofilm Formation on Urinary Catheters Inner Channel with SAW in an in Vitro Model.

Figure 20:
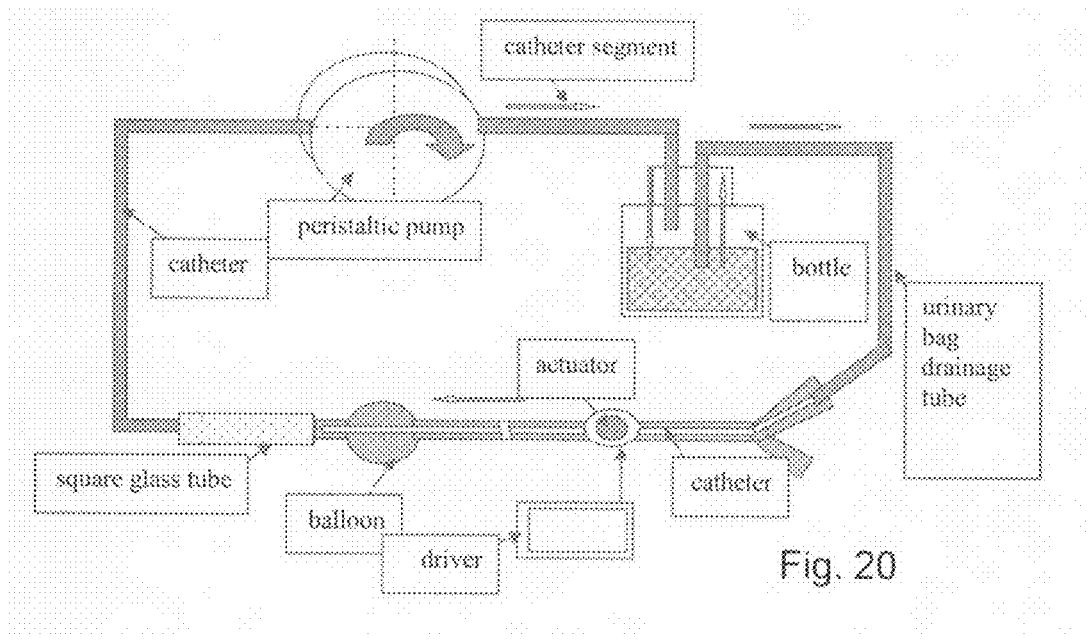
FIG. 20 shows an experimental in-vitro flow system for determining if surface acoustic waves generated by piezo actuators interferes with microbial biofilm formation on an inner channel of a urinary catheter.

The ultimate in vitro determination of whether SAW generating piezo actuators can interfere with microbial biofilm formation on urinary catheters inner channel was evaluated with specially designed flow system for this task test system The principle schematic representation of the experiment is shown in FIG. 20.

Figure 21:
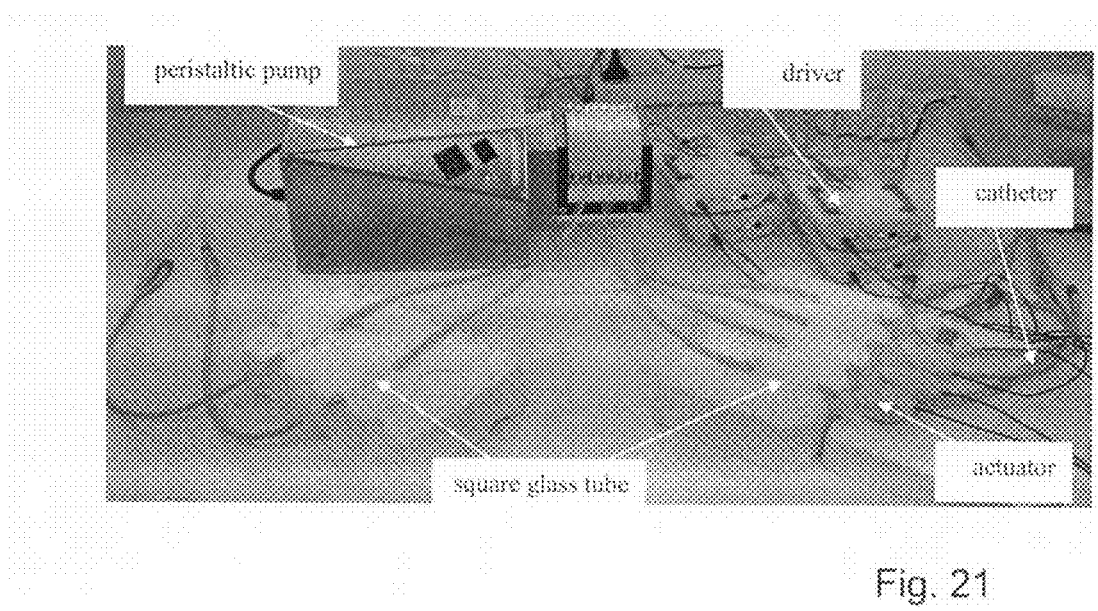
FIG. 21 is a view of an experiment comparing surface acoustic waves enhanced effect on biofilm formation, with silver coated catheters (Bard corporation), and regular Foley catheters.

The same system was used for comparison between SAW enhanced effect on biofilm formation, Bard silver coated catheters and regular Foley catheters. The experiment design is shown in FIG. 21.

A peristaltic pump is used for circulation in a closed loop flow system with rate of 0.2. A drainage tube of urinary bag is inserted into a glass feed flask containing 50 ml of synthetic urine with 15% of standard concentration BHI. The tube is connected to a urinary catheter which is connected to another catheter via a square glass tube. The distal catheter is connected to the Tygon tube of the peristaltic pump by a plastic connector. The other side of the Tygon tube is connected to a section of urinary catheter which is inserted to the same feed flask.

The actuators are attached to the catheter approximately 2 cm from the balloon upstream to the glass tubes. In the peristaltic pump, six channels are used, of which three channels are activated while the other three serve as control. A volume of 50 ml is circulated in each channel.

A bacterial suspension is prepared by inoculating Pseudomonas aeruginosa in LB broth (20 grams per liter of distilled sterile water) incubated overnight and diluted to obtain a required concentration. The bacterial suspension is counted and inoculated into the sterile media so as to contain circa $10^4$ CFU/ml. The duration of the experiment is seven days.

At the end of the experiment, the closed system is rinsed with ionized water in speed pump of 4.2 for 20 minutes approximately. After washing, the square glass tubes are removed and fixed in the oven at a temperature of 80° C. for 15 minutes, stained with crystal violet, rinsed and than inspected and photographed on an Olympus inverted microscope (CK40).

The results are shown in FIG. 22 A,B and FIG. 23A,B. Biofilm coverage: the activated lines are covered by biofilm less (22B) than square glass tubes from control group (22A). Square glass tubes from the activated line with Bard silver coated catheters channels are covered by biofilm less (23B) than the controls (23A). Note: only typical data for visual comparison is applied.

Prevention of Microbial Biofilm Formation by Surface Acoustic Waves

We examined the effects of the low-energy, high frequency SAW generated from electrically activated piezo elements on microbial biofilm formation on several types of surfaces including urinary catheters. The actuators were attached to 10 Fr Foley urinary catheters through which a medium containing several types of bacteria, which mimics conditions in the urinary bladder, was passed for seven days. FIGS. 24A,B show that SAW caused marked reductions in biofilm formation on the surface of these catheters. Analyses were then conducted on suspensions of ten most common clinically relevant bacteria using 16 Fr Foley catheters attached with SAW-generating piezo elements. Bacterial bioburden on surfaces of SAW-treated catheters measured by titration revealed an average reduction of $1.68 \pm 0.66$ $\log_{10}$ in bacterial biofilm load formed on surfaces of SAW treated catheters relative to controls (data not shown).

Figure 25A:
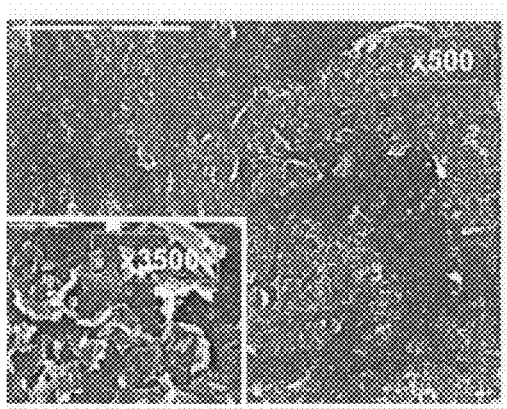
FIGS. 25A, 25B, 26A, 26B, 27A and 27B are scanning electron microscopic views obtained with *Candida albicans*, *Pseudomonas aeruginosa* and *Staphylococcus aureus* in control segments (FIGS. 25A, 26A, 27A) versus surface acoustic waves treated (FIGS. 25B, 26B, 27B).
Figure 25B:
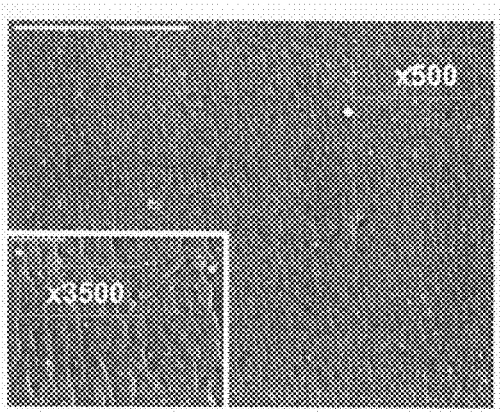
Figure 26A:
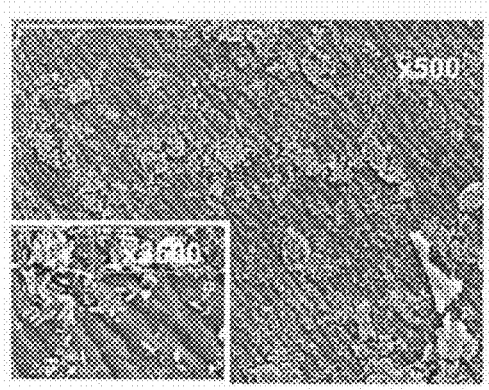
Figure 26B:
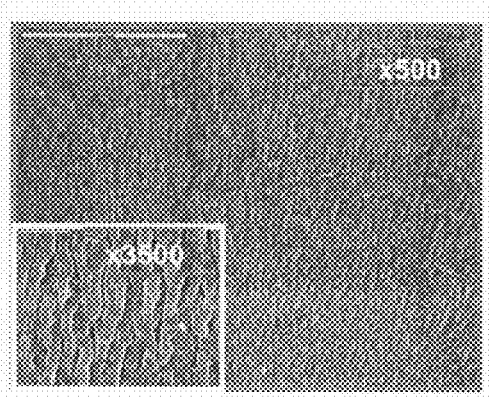
Figure 27A:
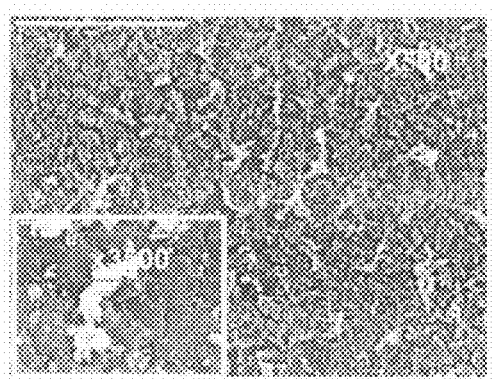
Figure 27B:
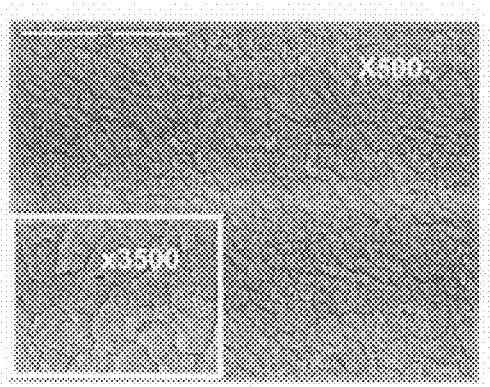

Other segments of these catheters were subjected to scanning electron microscopic analyses, and the results obtained with *Candida albicans, Pseudomonas aeruginosa* and *Staphylococcus aureus* are presented in FIGS. 25, 26, 27, namely the views of control segments (FIGS. 25A, 26A, 27A) versus SAW treated (FIGS. 25B, 26B, 27B). Marked reductions in biofilm formation leaving catheters virtually clean of adherent microorganisms are evident in the SAW treated urinary catheters irrespective of the types of bacteria that were examined. Similar reductions in biofilm deposition on glass rod surfaces attached with piezo actuators were also noted (data not shown), indicating that the piezo element-generated elastic waves can be adjusted to prevent microbial biofilm formation on surfaces of various consistencies and shapes.

Prevention of Microbial Biofilm Formation on Urinary Catheters with Acoustic Nanowave Actuators in an Animal Model in Vivo.

The ultimate preclinical determination of whether SAW generating piezo actuators can interfere with microbial biofilm formation on urinary catheters in clinical settings is in animal studies in vivo. We inserted 10 Fr Foley catheters to which a piezo actuator was attached at the extracorporeal portion of the catheter into the urinary bladders of male rabbits in a sterile manner. The devices were activated in four of eight tested rabbits (in three separate experiments) for up to nine days. Urine samples were collected daily, bacterial load quantified and time to bacteriuria determined. Urine from rabbits in which the catheters were treated with SAW remained sterile for 5, 7 and 9 days, (26 cumulative days of sterile urine) despite the extensive contamination of the perineal area with feces. Furthermore, the bacteriuria which did develop in some rabbits was mostly of low titres, whereas 3 of 4 control rabbits developed bacteriuria of $>10^6$ CFU/ml within 2-3 days and the fourth a titre of $>10^8$ CFU/ml on day seven. The average number of days to development of urinary tract infection, defined as bacteriuria of $>10^5$ CFU/ml, was $7.25 \pm 1.26$ days for the SAW treated animals versus $1.5 + 0.58$ days in the non treated controls ($p<0.0009$ in two tailed student T-test).

Figure 28A:
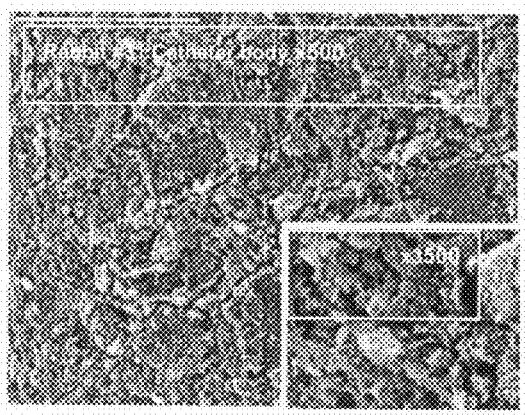
FIGS. 28A, 28B, 28C and 28D are scanning electron microscopy views of control group catheters.
Figure 28B:
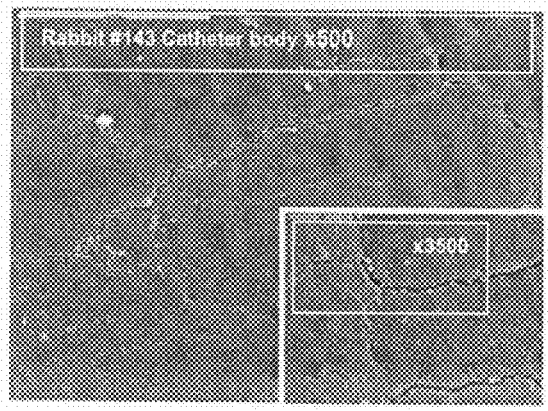
Figure 28C:
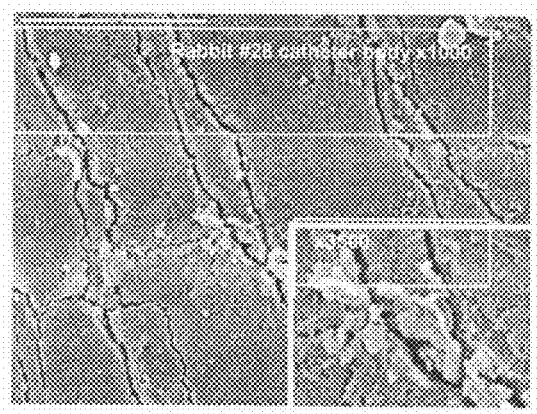
Figure 28D:
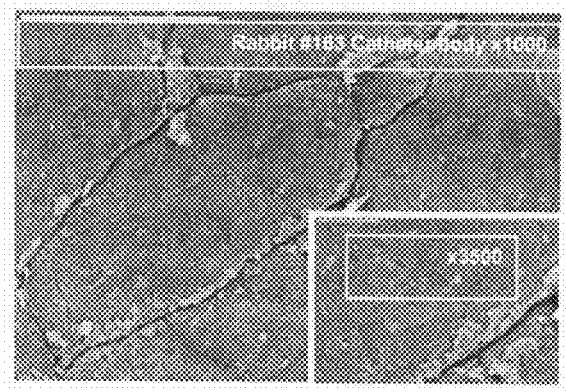

At termination of the experiments, the animals were sacrificed, the bladder and urethra opened, the catheters removed carefully avoiding shear force to prevent biofilms from being torn off. Biofilm content was examined by scanning electron microscopy. Analyses of the internal surfaces of recovered catheters reveal strong inhibition of bacterial biofilm formation on surfaces of catheters treated with SAW (see FIGS. 28B, 28D). In contrast, control group catheters were covered with varying densities of microbial biofilms despite the shorter durations of catheterization, which in two of the animals were in place for only 3-4 days (see FIGS. 28A, 28C)

Discussion

The remarkable flexibility by which microorganisms adapt to changing environments or become insulated from environmental hazards has been the core of shortcomings in the ability of chemical approaches to prevent microbial biofilm formation on implanted medical devices. Efforts to eradicate biofilms have therefore shifted to mechanical approaches, which thus far have mainly been aimed at increasing the penetration of antibiotics into microbial colonies.

We have contemplated utilization of mechanical approaches to interfere with early events in the biofilm development process—the adhesion of planktonic microorganisms to surfaces. By preventing adhesion we sought to abort their subsequent firm attachment to the substratum, the gene expression reprogramming and synthesis of the corresponding protein products that ensue, which transform the lifestyle of microorganisms from planktonic to the sessile form). We also speculate that chaotic streams produced in fluids by the ongoing high frequency vibrations hamper development of coherent concentration-dependent gradients of quorum sensing molecules. Disruption of such gradients is likely to interfere with cell-cell communications between microorganisms, virulence factor production and other post attachment biofilm developmental processes. The outcome is prevention of colony differentiation and biofilm formation.

We generate high frequency low energy elastic acoustic waves at non cavitational ranges from piezo actuators and transmit the waves directly to extracorporeal portions of implanted medical devices. These waves spread horizontally along the device surfaces and also propagate transversely. We show that these SAW interfere effectively with planktonic microorganism attachment to surfaces and prevent biofilm formation for extended time intervals. The mechanical nature of SAW implies that the elastic waves must be powered continuously throughout the duration of catheterization to prevent attachment of planktonic bacteria to implanted devices. Disruption of the vibration energy was found to enable renewed adhesion of bacteria to these surfaces. Resumption of SAW following disruption may prevent attachment of additional planktonic bacteria but has only limited effects on overall biomass of preformed biofilms. The purely mechanical effects of SAW are, thus, readily reversible and do not diminish the functionality of bacterial adhesion mechanisms such as the FimH lectin on uropathogenic *E. coli* fimbriae. Indeed, disruption of SAW allowed *E. coli* attachment to guinea pig RBC via FimH.

Another unique feature of our approach is the effectiveness of minute power intensities in preventing bacterial attachment to substrates. Analyses of mannose receptor-mediated adhesion of *E. coli* to guinea pig erythrocytes reveal that power densities ranging between 0.05-0.2 mW/cm$^2$ with amplitudes of ≦3 nanometers completely prevent erythrocyte aggregation. In contrast SAW intensities>0.35 mW/cm$^2$ generated opposite effects, inducing strong FimH-mediated adhesion of the bacteria and enhanced RBC aggregation. This bacterial response to high SAW intensities bears similarities to the response of these bacteria to shear stress. Under stress the FimH lectin acts as a force sensor switching bacterial loose adhesion into a firm attachment (16). Application of high SAW power intensities to *E. coli* bacteria co-cultured with guinea pig RBC also yielded a similar type of switching to enhanced erythrocyte aggregation.

We propose the following hypothesis to explain the low energy SAW-mediated biofilm prevention phenomenon. Attraction or repulsion of bacteria is an outcome of Van der Waals and hydrophobic attraction forces being counteracted by electrostatic repulsion in the 10 nm range near the surface. This phenomenon known as ??potential of the surface varies with the distance from the interface. SAW induced elliptical vibrations affect the surface and are transmitted through the surrounding fluid media causing the bacteria to vibrate with the same frequency. The amplitude at which the bacteria vibrate is smaller than that of the surface, it is governed by Stoke's law, and results in a relative velocity of bacteria respective to the surface. When the SAW-generated bacterial vibration amplitudes are smaller than the ??potential repulsive zone, an overall net repulsion occurs, preventing bacterial attachment. This is the hallmark of SAW. Increasing the bacteria vibration amplitudes to values exceeding the ??potential repulsion zone, and a net attraction force promotes the adhesion of bacteria, as observed at the higher SAW intensities. Such SAW intensities phenomenon activated bacteria docking and force sensor activity and this synergism can promote the increased adhesion of bacteria which we observed at the higher SAW intensities.

The studies which show that SAW reduces biofilm bioburden on catheter segments suspended with several gram negative and gram positive bacteria as well as fungi, indicate that the action of SAW is efficacious against a broad spectrum of microorganisms and not limited to selected groups. The studies in rabbits demonstrate the feasibility of delaying catheter associated urinary tract infections with SAW. These studies also show that SAW is unaffected by conditioning films encrusted with proteins, electrolytes and other organic molecules which develop on urinary catheters shortly after their insertion. This system may potentially be adapted to a variety of indwelling medical devices including endotracheal tubes, central venous or peritoneal dialysis catheters. The entire implanted medical device industry, including prosthetic joints and others, is likely to benefit from this approach.

Summary of the Clinical Trial

A double blind, comparative, randomized study for the safety evaluation of the add-on urinary catheter device was held in Heidelberg, Germany under the sponsorship of NanoVibronix Ltd. and completed in January 2006. The objectives were to demonstrate that the use of the device is safe to use in comparison with a siliconized latex urinary catheter (non active device), to demonstrate that the device is well tolerated by the patients and user friendly to the medical staff, and to demonstrate that the device helps in prevention of either bacteriuria or biofilm formation in comparison with the urinary catheter alone (i.e., non-active device).

Twenty-two hospitalized male patients, age 18 years or older, requiring a new catheterization for an estimated duration of ≧7 days, were randomly divided into two groups of eleven patients. One group was catheterized with a 14"-22" siliconized latex urinary catheter and the device attached thereto, and the second group were catheterized with just the 14"-22" siliconized latex urinary catheter.

With regard to safety, there was no striking single safety event related to the active device. Also, as a group the active group did not differ from the controls. Therefore it is concluded that the device is both safe and well tolerated. There were similar numbers of adverse events in both groups all classified as unrelated to the device. There was no evidence for different levels of discomfort, pain or irritation. Most of the daily scores were ranked (0) zero in a scale zero (0) to five (5). During days 1-4, three (3) patients in the control group and 1 in the active group ranked discomfort at the level of 1-2 (out of 5). After day 5 of the hospitalization, no patients reported any discomfort ranked as 2 or higher.

With regard to efficacy, the number experiencing positive urine culture was similar in both groups, three in the control group and four in the active group. These numbers also meets the expected prevalence as reported by others; that is four cases per group.

However, as expected, the sample size in this study was too small to study the efficacy of the device. Antibiotic administration was similar in both groups. An analysis of medications related to management of Foley Catheter pain and discomfort revealed that the active subjects required less medication than the control group. Scanning electron microscopy of the catheters revealed that there was no biofilm in the treated group as compared to the seven control catheters found with biofilm.

Thus, a urinary catheter clip-on device for applying surface acoustic waves to a urinary catheter for preventing biofilms on the catheter surfaces has been provided. One skilled in the art will appreciate that the present invention can be practiced by other than the described embodiments, which are presented for purposes of illustration and not limitation. Further, since numerous modifications and changes will readily occur to those skilled in the art, it is not desired to limit the invention to the exact construction and operation shown and described, and accordingly, all suitable modifications and equivalents may be resorted to, without departing from the scope or spirit of the invention as defined in the appended claims.

The invention claimed is:

1. A device for preventing catheter associated urinary tract infections on a urinary catheter positioned at least partially within a patient's body, the device comprising:
   a catheter,
   an actuator coupled to the catheter at a location outside of the patient's body, wherein said actuator comprises a housing formed of two opening housing parts, a first of said parts containing springing material attached to an internal surface thereof and the second of said parts containing a piezo resonator element, wherein said piezo resonator element is attached to said springing material by means of gluing tape, and the gluing tape is attached to the external surface of said piezo resonator element and is coupled to the external surface of the urinary catheter, and
   a driver electrically connected between said actuator and said catheter,
   whereby the actuator generates acoustic surface waves of Rayleigh—Lamb or Love type, or both, on the catheter and transmits acoustic surface waves around the catheter surface in the direction towards the patient's body, whereby the surface waves mechanically create relative oscillation velocity of bacteria in relation to the catheter surface to thereby prevent their attachment to the catheter surfaces.

2. The device according to claim 1, wherein the surface wave-generated bacterial relative elliptical oscillation amplitudes are smaller than the potential repulsive zone, an overall net repulsion occurs, being effective in:
   inhibiting bacteria attachment to urinary catheter surfaces,
   inhibiting adhesion, growth and aggregation of cells into micro colonies on urinary catheter surfaces; and
   inhibiting maturation and dissemination of progeny cells for new colony formation.

3. The device according to claim 1, wherein said surface acoustic waves have mechanical amplitudes in the range from about 0.1 nanometers to about 5 nanometers.

4. The device according to claim 3, wherein the velocity of said wave is about 14 m/s to about 30 m/s, and said velocity magnitudes being close to the acoustic wave velocity in the skin, such that the created acoustic wave does not additionally irritate the skin tissue.

5. The device according to claim 1, wherein the actuator creates an acoustic energy transmission lines towards the liquid and body tissues in acoustic contact with urinary catheter, which may have two components:
   a) at a depth equal to two surface wave lengths towards the body tissues, the tissue particles are mechanically-elliptically oscillating, with a velocity of tenths of a meter/second;
   b) at a the depth exceeding two surface wave lengths towards the body tissues, the tissue particles are lineally-mechanically oscillating, with nanometer amplitudes;
   which thereby result in positive effects on tissues, followed by one or more of the following: increased repair and healing processes, increased growth of capillary, increased ph of tissue liquids, lowered pain syndrome, and micro massaging.

6. The device according to claim 5, wherein said urinary catheter is coated on an internal or external surface thereof, or on both surfaces thereof, by copper or silver alloy, silver hydrogel, antibiotic coat, or any other antimicrobial coat, and the balloon resonance thereby increases antimicrobial action on tissue healing processes in addition to preventing bacteria adhesion and biofilm formation on these antimicrobial surfaces and increasing antimicrobial action time of the coating agents.

7. The device according to claim 1, further comprising an additional vibration energy source from balloon resonance.

8. The device according to claim 7, wherein balloon vibrations are excited due to longitudinal type waves transmitted through liquids filling the inflation channel of the balloon and exciting balloon resonance resulting from actuator oscillations in the same frequency as the natural balloon self resonance frequency.

9. The device according to claim 8, wherein the acoustic energy generated by said balloon exceeds by about 5 to about 10 times the surface acoustic energy excited on the catheter surface by said actuator, and the ranges of balloon mechanical vibration amplitudes are from about 0.5 to about 5.0 nm.

10. The device according to claim 9, wherein part of said acoustic surface wave has a transversal vector of up to about 5 cm and whereby biofilm formation is prevented not only on the catheter surface but also on human tissue in adjacent contact with the catheter.

11. The device according to claim 10, wherein the controlling of balloon pressure and shape comprises obtaining directional and focused acoustic energy from balloon to body tissues in contact with it, by this action controlled therapeutic effect may be applied.

12. The device according to claim 7, wherein the electric pulses produce piezoelectric effects which generate high frequency micro-mechanical vibration energy in the actuator at frequencies of from about 100 to about 500 kHz with acoustic intensity of 200 mW/cm2 and amplitudes of 300-800 nanometers.

13. The device according to claim 1, wherein said driver comprises a controller with power supply, a central processing unit with memory, alarm indicators and oscillator of pulsed or harmonic signals for generating electrical signals which are transformed to actuator.

14. The device according to claim 1, wherein said alarm indicators comprise one or more of a power indicator, low battery circuit, low voltage circuit alarm visual indicator, and an acoustic indicator.

15. The device according to claim 1, wherein said piezo resonator transforms electrical signals to mechanical vibrations which excite surface acoustic waves having mechanical vibration amplitudes of from about 0.1 to about 0.3 nm, said surface waves propagating along the catheter surface.

16. The device according to claim 15, wherein said piezo resonator is a disk-shaped thin piezo ceramic element with electrodes.

17. The device according to claim 16, wherein the vibrations of said actuator piezo element may be applied in multi-modes chosen from thickness, longitudinal, and a combination thereof.

18. The device according to claim 16, wherein the acoustic energy is achieved with at least one disk shaped piezo element having dimensions: 26×26×0.10 (mm).

19. The device according to claim 18, wherein said piezo resonator element is coated with a silver electrode on one side and with a thin metallic layer on the other side, and the diameter of said metallic layer should be equal to or exceed the piezo element diameter.

20. The device according to claim 16, wherein the range of the piezo ceramic oscillations frequencies is from about 1 Hz to about 10 MHz.

21. The device according to claim 16, wherein the distances between max or min vibration amplitudes points of the piezo element must be equal to half surface acoustic wave length excited on the catheter material.

22. The device according to claim 16, wherein the waves are generated in a longitudinal and bending vibration modes by a piezo resonator having a polarization axis perpendicular to the surface of the catheter.

23. The device according to claim 16, wherein the waves are generated by a piezo ceramic material joined to a metal material into a bimorph element, each material being present in a layer at a respective thickness ratio of about 0.95 to about 1.35.

24. The device according to claim 16, wherein said electrodes have non-conductive portions, which may be parallel or non-parallel to the direction of polarization, and the single phase, two-phase or multi phase electrical signal may be sent from said driver to said electrodes, and
   wherein, by means of different connections between electrodes longitudinal, bending and thickness vibrations may be excited simultaneously or separately.

25. The device according to claim 1, wherein said piezo resonator element is coupled to the catheter via stabilizing needles for better acoustic energy transfer and elimination of actuator slipping.

26. The device according to claim 1, further comprising a second driver for supplying electric signals to the piezo element, the signals being selected from at least one of the following group: megahertz frequency signals, kilohertz frequency signals and of electric signals forms and duty cycles, and combinations thereof.

27. The device according to claim 26, wherein said second driver is integrated into the actuator as a chip.

28. The device according to claim 26, whereby the actuator applies short-term stress so as to dislodge the bacteria from the catheter surface.

29. The device according to claim 1, wherein the particles and bacteria on the catheter surface are forced in a direction opposite to the direction of vibration transmission, thereby preventing bacteria propagation extraluminally and forcing said bacteria out of the patient's body.

30. The device according to claim 1, wherein the energy of said acoustic surface waves has a transverse character, such that the energy may be transferred to the tissues of the human body from an external surface thereof and transferred to urine from the internal surface of the catheter, thus preventing bacteria propagation intraluminally.

31. The device according to claim 30, wherein said transverse vibration energy affects the fluids upon contact and the friction of the fluids is reduced, whereby the vibration may expel the fluid and drying process at the point of contact with the body, which slows or prevents the entry of bacteria extraluminally.

32. The device according to claim 1, wherein mechanical vibration energy is generated by a piezo element, achieving the pushing or pulling of fluids and particulates suspended therein along the surfaces of the catheter.

33. The device according to claim 1, wherein vibrational energy of said acoustic surface waves is of a kind sufficient to stimulate or release nitric oxide from at least small areas of targeted organs or tissues.

34. The device according to claim 1 wherein acoustic surface waves induced on urinary catheter material prevent bacteria virulence occurrence and result in antibiotic use reduction for treatment.

35. The device according to claim 1, wherein vibrational energy of said acoustic surface waves reduces existing biofilm, augments the effectiveness of antibiotics against the biofilm and produces antimicrobial and antithrombogenic surfaces.

36. The device according to claim 1, wherein acoustic surface waves induced micro streaming and affect in wound healing process.

37. The device according to claim 1, wherein vibrational energy of said acoustic surface waves inhibits infections of inner organs in acoustic contact with catheter.

38. The device according to claim 1, wherein vibrational energy of said acoustic surface waves increases slipping of the catheter and lowers coefficient of friction, thereby preventing injury, irritation, inflammation, ensuring less pain and less trauma to the patient and facilitating medical and surgical procedures.

39. The device according to claim 1, wherein said urinary catheter is coated on an internal or external surface thereof, or on both surfaces thereof, by copper, silver alloy, silver hydrogel, antibiotic coat, or any other antimicrobial coat, and said device thereby prevents bacteria adhesion and biofilm formation on these antimicrobial surfaces, increasing antimicrobial action time of the coating agents.

40. The device according to claim 39, wherein said surface acoustic waves are applied in the interface between catheter material surface and coating layers, thereby influencing on antimicrobial agent activeness, controlling the velocity and time of this agent's diffusion.

41. The device according to claim 39, wherein said surface acoustic waves are applied in the interface between said catheter coating layer and body tissues, thereby resulting in prevention of contaminations from occurring on the surface and thus increasing antimicrobial action time of the coating agents, increasing antimicrobial agent activeness, controlling the velocity and time of this agent's diffusion.

42. The device according to claim 39, wherein said surface acoustic waves are applied in two interfaces: between catheter material surface and coating layers and between said catheter coating layer and body tissues, thereby resulting in prevention of contaminations to occur on the surface and thus increasing antimicrobial action time of the coating agents, increasing antimicrobial agent activeness, controlling the velocity and time of this agent's diffusion.

43. The device according to claim 1, wherein the catheter is manufactured from materials including: silicone rubber, Teflon®, polyethylene (PE), polypropylene (PP), polyvinyl chloride (PVC), polyurethane (PU), polytetrafluoroethylene (PTFE), Nylon®, polyethylene terephthalate (PET), and glass, the said materials being used alone or with different coats.

44. The device according to claim 1, wherein the catheter is manufactured from materials with enhanced surface area substrates such as nanofiber substrates, other riffled surfaces.

45. The device according to claim 1, wherein said actuator lowers the coefficient of friction of said catheter surface, thereby prevent injury, irritation, or inflammation to the patient and to facilitate medical and surgical procedures.

46. The device according to claim 1, wherein said actuator is attached to the patient's leg with a specially designed securement system.

47. The device according to claim 1, wherein said actuator is incorporated into a detachable patch that can be secured to said patient's leg, and is connected to either a disposable or nondisposable energy source and said driver.

48. The device according to claim 1, wherein said surface acoustic waves have frequencies in the range from about 100 KHz to about 1 MHz.

49. The device according to claim 1, wherein said surface acoustic waves are of running wave type.

50. A device for creating surface acoustic waves when positioned on a catheter at least partially within a patient's body, the device comprising:
an actuator coupled to the catheter at a location outside of the patient's body, wherein said actuator comprises a housing formed of two opening housing parts, a first of said parts containing springing material attached to an internal surface thereof and the second of said parts containing a piezo resonator element, said actuator containing a piezo resonator element which is attached to said springing material by means of gluing tape, and the gluing tape is attached to the external surface of said piezo resonator element and said piezo resonator is coupled to the external surface of the catheter, and
a driver electrically connected with said actuator,
whereby the surface acoustic waves mechanically affect the catheter material and tissues which are in contact with the catheter.

* * * * *